(12) United States Patent
Jain et al.

(10) Patent No.: US 9,133,116 B2
(45) Date of Patent: Sep. 15, 2015

(54) BICYCLIC COMPOUNDS

(75) Inventors: Rajesh Jain, New Delhi (IN); Sanjay Trehan, New Delhi (IN); Jagattaran Das, New Delhi (IN); Nishan Singh, New Delhi (IN); Sudhir Kumar Sharma, New Delhi (IN)

(73) Assignee: PANACEA BIOTEC LTD., New Delhi (IN)

( * ) Notice: Subject to any disclaimer, the term of this patent is extended or adjusted under 35 U.S.C. 154(b) by 246 days.

(21) Appl. No.: 13/876,757

(22) PCT Filed: Sep. 27, 2011

(86) PCT No.: PCT/IN2011/000669
§ 371 (c)(1),
(2), (4) Date: Jun. 10, 2013

(87) PCT Pub. No.: WO2012/042539
PCT Pub. Date: Apr. 5, 2012

(65) Prior Publication Data
US 2013/0253029 A1  Sep. 26, 2013

(30) Foreign Application Priority Data

Sep. 28, 2010 (IN) ............................. 2322/DEL/2010
May 26, 2011 (IN) ............................. 1515/DEL/2011

(51) Int. Cl.
| C07D 209/52 | (2006.01) |
| A61K 31/403 | (2006.01) |
| A61K 45/06 | (2006.01) |

(52) U.S. Cl.
CPC ............ *C07D 209/52* (2013.01); *A61K 31/403* (2013.01); *A61K 45/06* (2013.01)

(58) Field of Classification Search
None
See application file for complete search history.

(56) References Cited

U.S. PATENT DOCUMENTS

| 4,435,419 A | 3/1984 | Epstein |
| 4,438,130 A | 3/1984 | Kaplan |
| 5,164,402 A | 11/1992 | Brighty |
| 5,475,116 A | 12/1995 | Brighty |
| 5,703,091 A | 12/1997 | Steiner |
| 5,968,929 A | 10/1999 | Blythin |
| 6,313,312 B1 | 11/2001 | Banks |
| 2003/0207876 A1 | 11/2003 | Banks |
| 2003/0232739 A1 | 12/2003 | Lowe, III |
| 2004/0002504 A1 | 1/2004 | Chambers |
| 2004/0147760 A1 | 7/2004 | Thomas |
| 2005/0075387 A1 | 4/2005 | Tickner |
| 2007/0082939 A1 | 4/2007 | Lippa |
| 2008/0176860 A1 | 7/2008 | Weber |
| 2009/0075970 A1 | 3/2009 | Edwards |
| 2009/0270364 A1 | 10/2009 | Liu |

FOREIGN PATENT DOCUMENTS

| EP | 0 129 991 A1 | 2/1985 |
| EP | 0 413 455 A2 | 2/1991 |
| EP | 0 747 355 A1 | 11/1996 |
| EP | 1980150 A1 | 10/2008 |
| JP | 2009040709 A | 2/2009 |
| WO | 9515327 | 8/1995 |
| WO | 97/19942 A1 | 6/1997 |
| WO | 97/36871 A1 | 10/1997 |
| WO | 97/36906 A1 | 10/1997 |
| WO | 00/39089 A1 | 7/2000 |
| WO | 0198267 | 12/2001 |
| WO | 02/34716 A2 | 5/2002 |
| WO | 02/066427 A2 | 8/2002 |

(Continued)

OTHER PUBLICATIONS

Hyo-Kyung Han, Target Prodrug Design to Optimize Drug Delivery, AAPS Pharmsci 2000; 2 (1) article 6 (http://www.pharmsci.org/), Mar. 21, 2000, pp. 1-11, Parke-Davis Pharmaceutical Research, Division of Warner-Lambert, Department of Pharmacokinetics, Dynamics and Metabolism, 2800 Plymouth Road, Ann Arbor, Michigan 48105, USA.

(Continued)

*Primary Examiner* — Michael Barker
(74) *Attorney, Agent, or Firm* — Lowe Hauptman & Ham, LLP

(57) ABSTRACT

The present invention relates to novel compounds of Formula I, their pharmaceutically acceptable derivatives, tautomeric forms, isomers, polymorphs, prodrugs, metabolites, salts or solvates thereof. The invention also relates to processes for the synthesis of novel compounds of Formula I, their pharmaceutically acceptable derivatives, tautomeric forms, isomers, polymorphs, prodrugs, metabolites, salts or solvates thereof. The present invention further provides pharmaceutical compositions comprising compounds of Formula I and methods of treating or preventing one or more disorders of the central and/or peripheral nervous system, preferably by modulating neurological and/or psychiatric targets (GPCR and/or non-GPCR).

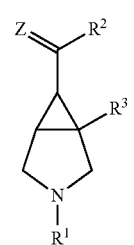

Formula I

20 Claims, No Drawings

(56) References Cited

FOREIGN PATENT DOCUMENTS

| | | |
|---|---|---|
| WO | 03/027083 A1 | 4/2003 |
| WO | 03/035622 A1 | 5/2003 |
| WO | 2004/004629 A2 | 1/2004 |
| WO | 2004/014363 A1 | 2/2004 |
| WO | 2004/018422 A1 | 3/2004 |
| WO | 2004/033451 A1 | 4/2004 |
| WO | 2004/056810 A1 | 7/2004 |
| WO | 2004/089364 A1 | 10/2004 |
| WO | 2004/089943 A1 | 10/2004 |
| WO | 2005/005398 A2 | 1/2005 |
| WO | 2005/005399 A1 | 1/2005 |
| WO | 2005/005420 A1 | 1/2005 |
| WO | 2005/005422 A1 | 1/2005 |
| WO | 2005/026121 A1 | 3/2005 |
| WO | 2005/037216 A2 | 4/2005 |
| WO | 2005/037790 A1 | 4/2005 |
| WO | 2005/087731 A1 | 9/2005 |
| WO | 2005/117872 A2 | 12/2005 |
| WO | 2006/002133 A1 | 1/2006 |
| WO | 2006/024955 A1 | 3/2006 |
| WO | 2006/032466 A2 | 3/2006 |
| WO | 2006/054162 A1 | 5/2006 |
| WO | 2006064304 A1 | 6/2006 |
| WO | 2006/096810 A2 | 9/2006 |
| WO | 2006/106425 A1 | 10/2006 |
| WO | 2006/117754 A1 | 11/2006 |
| WO | 2006/123121 A1 | 11/2006 |
| WO | 2007/006117 A1 | 1/2007 |
| WO | 2007/007282 A2 | 1/2007 |
| WO | 2007/014264 A2 | 2/2007 |
| WO | 2007/016155 A2 | 2/2007 |
| WO | 2007/127421 A2 | 11/2007 |
| WO | 2007/135527 A2 | 11/2007 |
| WO | 2007/135529 A2 | 11/2007 |
| WO | 2007/138431 A2 | 12/2007 |
| WO | 2008/013856 A2 | 1/2008 |
| WO | 2008/029349 A2 | 3/2008 |
| WO | 2008/053131 A1 | 5/2008 |
| WO | 2008/074716 A1 | 6/2008 |
| WO | 2008/075162 A2 | 6/2008 |
| WO | 2008/084300 A1 | 7/2008 |
| WO | 2008/117229 A1 | 10/2008 |
| WO | 2008/153937 A2 | 12/2008 |
| WO | 2009/027293 A1 | 3/2009 |
| WO | 2009/090548 A2 | 7/2009 |
| WO | 2009/141412 A1 | 11/2009 |
| WO | 2010/013222 A1 | 2/2010 |
| WO | 2010/025890 A1 | 3/2010 |
| WO | 2010/150281 A2 | 12/2010 |

OTHER PUBLICATIONS

Hiroshi Imoto, "Studies on Non-Thiazolidinedione Antidiabetic Agents. 2.1) Novel Oxyiminoalkanoic Acid Derivatives as Potent Glucose and Lipid Lowering Agents," Chem. Pharm. 51(2) 138-151 (2003), Nov. 8, 2002, pp. 1-4, vol. 51, No. 2, Takeda Chemical Industries, Ltd., Pharmaceutical Research Division; Feb. 17, 1985, Juso-Honmachi, Yodogawa-ku, Osaka 532-8686, Japan.

Xia Li, "Metabotropic Glutamate 5 Receptor Antagonism Is Associated with Antidepressant-Like Effects in Mice," The Journal of Pharmacology and Experimental Therapeutics, Jun. 23, 2006, pp. 1-6 Neuroscience Discovery Research, Lilly Research Laboratories, Eli Lilly & Co., Indianapolis, Indiana.

Anandan Palani, "Synthesis, SAR, and Biological Evaluation of Oximino-Piperidino-Piperidine Amides. 1. Orally Bioavailable CCR5 Receptor Antagonists with Potent Anti-HIV Activity," Journal of Medicinal Chemistry, 2002, vol. 45, No. 14, pp. 3143-3160, Feb. 19, 2002, Chemical Research, Drug Research, Drug Safety and Metabolism, and Antiviral Research, Schering-Plough Research Institute, 2015 Galloping Hill Road, Kenilworth, New Jersey 07033.

Stacie S. Canan Koch, Synthesis of Retinoid X Receptor-Specific Ligands That Are Potent Inducers of Adipogenesis in 3T3-L1 Cells, Journal of Medicinal Chemistry, 1999, vol. 42, No. 4, pp. 742-750, Feb. 5, 1999, Departments of Medicinal Chemistry, Retinoid Research, and New Leads Discovery, Ligand Pharmaceuticals, Incorporated, 10255 Science Center Drive, San Diego, California 92121.

W.L.F. Armarego, "Purification of Laboratory Chemicals," Fourth Edition, Butterworth Heinemann, pp. 67-68, 176, 192-193, 199-200, 332 (1996).

Katherine E. Brighty, "Synthesis of (1a,5a,6a)-6-Amino-3-azabicyclo[3.1.0]hexane, a Novel Achiral Diamine," Department of Medicinal Chemistry, Box 39, Building 118W, Pfizer Central Research, Eastern Point Road, Groton, CT 06340, USA, Nov. 1996, pp. 1097-1099.

Theodora W. Greene, "Protective Groupd in Organic Synthesis," Third Edition, John Wiley & Sons, Inc. pp. 518-525, 531-537 (1981).

BICYCLIC COMPOUNDS

RELATED APPLICATIONS

The present application is the U.S. National Stage of PCT/IN2011/000669, filed Sep. 27, 2011, Published in English, which application claims priority from 2322/DEL/2010 filed Sep. 28, 2010 and 1515/DEL/2011 filed May 26, 2011

FIELD OF THE INVENTION

The present invention relates to novel compounds of Formula I, their pharmaceutically acceptable derivatives, tautomeric forms, isomers, polymorphs, prodrugs, metabolites, salts or solvates thereof. The invention also relates to processes for the synthesis of novel compounds of Formula I, their pharmaceutically acceptable derivatives, tautomeric forms, isomers, polymorphs, prodrugs, metabolites, salts or solvates thereof. The present invention further provides pharmaceutical compositions comprising compounds of Formula I and methods of treating or preventing one or more disorders of the central and/or peripheral nervous system, preferably by modulating neurological and/or psychiatric targets (GPCR and/or non-GPCR).

BACKGROUND OF THE INVENTION

The present invention is directed to compounds useful for treating or preventing one or more disorders, preferably disorders of the central and/or peripheral nervous system. The disorders include depression, psychotic disorders, mood disorders, bipolar disorders, personality disorders, eating disorders, aggressive behavior, schizophrenia, inflammatory bowel disorders, irritable bowel syndrome, pain, chronic neuropathic pain, addiction disorders including cocaine abuse, urinary incontinence, dementia, Alzheimer's memory loss, Parkinsonism, stroke, anxiety, attention-deficit disorder, social phobia, pathological crying and/or laughing, obsessive compulsive disorder, substance (like nicotine, alcohol and opium) abuse and withdrawal (substance related disorder), cognitive disorders, fibromyalgia, Interstitial cystitis, Nocturnal enuresis, Ciguatera poisoning, Body dysmorphic disorder, Lichen simplex chronicus, chronic hiccups and sleep disorders. Included among these disorders are disorders related to depression, such as pseudodementia, migraine pain or headache, bulimia, obesity, pre-menstrual syndrome or late luteal phase syndrome, tobacco abuse, smoking, panic disorder, memory loss, dementia of ageing, acquired immunodefeciency syndrome dementia complex, memory dysfunction in ageing, anti-attention deficit hyperactivity disorder (ADHD), chronic fatigue syndrome, premature ejaculation, erectile difficulty, anorexia nervosa, narcolepsy, Gilles de la Tourettes disease, presenile dementia, senile dementia, cognition impairment, sexual dysfunctions, disorders of sleep or autism, mutism or trichotillomania.

The pathophysiology of major depression is poorly understood being a multifactorial syndrome. The increase in the number of individuals with some or other form of central and/or peripheral nervous system disorders has resulted in tremendous efforts towards the development of drugs for central and/or peripheral nervous system. Several classes of drugs with a range of binding selectivities have been discovered and used in the treatment of various central and/or peripheral disorders. The activity of earlier drugs was due to their binding to a broad range of neurotransmitter receptors/re-uptake proteins which led to many undesirable side effects along with considerable delay in the onset of relief. These drugs are not able to meet the treatment goals, have variable response in patients and do not have a favorable profile in modulating neurological and/or psychiatric targets (GPCR and/or non-GPCR).

Azabicyclohexane derivatives are extensively known in the prior art particularly for the treatment of central and/or peripheral nervous system disorders. For example The PCT applications WO 2010025890, WO 2010150281, WO 2010013222, WO 2009090548, WO 2009027293, WO 2009141412, WO 2008117229, WO 2008013856, WO 2008153937, WO 2008075162, WO 2008074716, WO 2008029349, WO 2008053131, WO 2008084300, WO 2007135529, WO 2007127421, WO 2007006117, WO 2007138431, WO 2007016155, WO 2007014264, WO 2007007282, WO 2007135527, WO 2006024955, WO 2006054162, WO 2006064304, WO 2006096810, WO 2006106425, WO 2006117754, WO 2006123121, WO 2006032466, WO 2006002133, WO 2005037790, WO 2005037216, WO 2005005399, WO 2005117872, WO 2005005422, WO 2005005420, WO 2005005398, WO 2005087731, WO 2005026121, WO 2004033451, WO 2004004629, WO 2004014363, WO 2004018422, WO 2004056810, WO 2004089364, WO 2004089943, WO 2003035622, WO 2003027083, WO 2002066427, WO 2002034716, WO 200198267, WO 2000039089, WO 9719942, WO 9736906, WO 9736871 and WO 199515327 disclose azabicyclohexane derivatives, some of which are useful for the treatment of central and/or peripheral nervous system disorders. Similarly, the following applications/patents: US 20090075970, US 20090270364, US 20080176860, US 2005075387, US 20040002504, US 20040147760, US 2003232739, US 20030207876, US 2003207876, US 20030207876, U.S. Pat. No. 6,313,312, U.S. Pat. No. 5,968,929, U.S. Pat. No. 5,475,116, U.S. Pat. No. 5,164,402, U.S. Pat. No. 4,435,419, U.S. Pat. No. 4,435,419, U.S. Pat. No. 4,438,130, EP 1980150, EP 0747355, EP 413455, EP 0129991 and JP2009040709, also disclose azabiclyclohexane derivatives.

Although a number of azabicyclohexane derivatives are described in the art there is an ongoing need for the development of effective and safe compounds for treatment of central and/or peripheral nervous system disorders. Depending upon the selection of different types of substituents on the main scaffold "3-azabicyclohexane", the specificity or affinity for the different neurological and/or psychiatric targets (GPCR and/or non-GPCR) varies. Thus, it would be advantageous to provide further neurological and/or psychiatric target (GPCR and/or non-GPCR) modulators which can become potential drugs for central and/or peripheral nervous system disorders. The compounds of the present invention are structurally different from the known 3-azabicyclohexane derivatives. These may advantageously possess characteristics such as favorable profile towards modulating different neurological and/or psychiatric targets (GPCR and/or non-GPCR), enhanced potency and/or minimum side effects.

SUMMARY OF THE INVENTION

The present invention relates to the novel compounds of the Formula I,

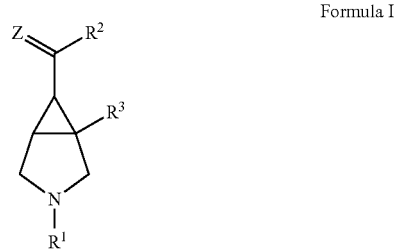

Formula I their pharmaceutically acceptable derivatives, tautomeric forms, isomers, polymorphs, prodrugs, metabolites, salts or solvates thereof, wherein:

$R^1$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl or heteroaryl; each of which may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a(C=NR^b)NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a(=NOR^b)$, —$CR^a(=NCOOR^b)$, —$CR^a(=NSOR^b)$, —$CR^a(=NSO_2R^b)$, —C(=$NR^a$)—$NR^bR^c$, —C(=$NOR^a$)—$NR^bR^c$, —$CR^a(=NCN)$, —$NCR^a$, —$P(O)R^aR^b$, —$P(O)OR^aOR^b$, —$P(O)R^aOR^b$, —$P(O)NR^aOR^b$, —$P(O)NR^aR^b$, —$OP(O)R^aR^b$ or —NHP(O)$R^aR^b$;

with the proviso that when $R^1$ is heterocyclyl, aryl or heteroaryl, then the said heterocyclyl, aryl or heteroaryl cannot be substituted with heterocyclyl;

$R^2$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl or heteroaryl; each of which may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a(C=NR^b)NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a(=NOR^b)$, —$CR^a(=NCOOR^b)$, —$CR^a(=NSOR^b)$, —$CR^a(=NSO_2R^b)$, —C(=$NR^a$)—$NR^bR^c$, —C(=$NOR^a$)—$NR^bR^c$, —$CR^a(=NCN)$, —$NCR^a$, —$P(O)R^aR^b$, —$P(O)OR^aOR^b$, —$P(O)R^aOR^b$, —$P(O)NR^aOR^b$, —$P(O)NR^aR^b$, —$OP(O)R^aR^b$ or —NHP(O)$R^aR^b$;

$R^3$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl or heteroaryl; each of which may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a(C=NR^b)NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a(=NOR^b)$, —$CR^a(=NCOOR^b)$, —$CR^a(=NSOR^b)$, —$CR^a(=NSO_2R^b)$, —C(=$NR^a$)—$NR^bR^c$, —C(=$NOR^a$)—$NR^bR^c$, —$CR^a(=NCN)$, —$NCR^a$, —$P(O)R^aR^b$, —$P(O)OR^aOR^b$, —$P(O)R^aOR^b$, —$P(O)NR^aOR^b$, —$P(O)NR^aR^b$, —$OP(O)R^aR^b$ or —NHP(O)$R^aR^b$;

provided that
(a) atleast one of $R^2$ and $R^3$ is aryl or heteroaryl
(b) when $R^3$ is aryl or heteroaryl, then $R^3$ cannot be substituted by heterocyclyl;

Z represents either $NOR^4$ or $NNR^4R^5$;

$R^4$ and $R^5$ are independently selected from —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl or heteroaryl; each of which may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a(C=NR^b)NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a(=NOR^b)$, —$CR^a(=NCOOR^b)$, —$CR^a(=NSOR^b)$, —$CR^a(=NSO_2R^b)$, —C(=$NR^a$)—$NR^bR^c$, —C(=$NOR^a$)—$NR^bR^c$, —$CR^a(=NCN)$, —$NCR^a$, —$P(O)R^aR^b$, —$P(O)OR^aOR^b$, —$P(O)R^aOR^b$, —$P(O)NR^aOR^b$, —$P(O)NR^aR^b$, —$OP(O)R^aR^b$ or —NHP(O) $R^aR^b$;

or $R^4$ and $R^5$ are joined together to form a heterocyclyl;

with the proviso that when Z is $NOR^4$, and $R^4$ is $C_{1-12}$ alkyl, then $R^2$ cannot be heterocyclyl or heteroaryl;

$R^a$, $R^b$, $R^c$ and $R^d$ are independently selected from —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH) or —CH(=NCN); wherein alkyl, alkenyl, alkynyl, cycloalkyl, cycloalkenyl, cycloalkynyl, heterocyclyl, aryl and heteroaryl groups may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH) or —CH(=NCN);

or $R^a$ and $R^b$ are joined together to form a $C_{3-7}$ cycloalkyl, $C_{3-7}$ cycloalkenyl, $C_{6-8}$ cycloalkynyl, heterocyclyl, aryl or heteroaryl;

or $R^b$ and $R^c$ are joined together to form a $C_{3-7}$ cycloalkyl, $C_{3-7}$ cycloalkenyl, $C_{6-8}$ cycloalkynyl, heterocyclyl, aryl or heteroaryl;

or $R^c$ and $R^d$ are joined together to form a $C_{3-7}$ cycloalkyl, $C_{3-7}$ cycloalkenyl, $C_{6-8}$ cycloalkynyl, heterocyclyl, aryl or heteroaryl.

Another aspect of the invention provides processes for the preparation of the novel compounds of Formula I, their pharmaceutically acceptable derivatives, tautomeric forms, isomers, polymorphs, prodrugs, metabolites, salts or solvates thereof.

A further aspect of the present invention provides pharmaceutical compositions, containing compounds of Formula I, their pharmaceutically acceptable derivatives, tautomeric forms, isomers, polymorphs, prodrugs, metabolites, salts or solvates thereof in combination with one or more pharmaceutically acceptable carrier(s), adjuvants and vehicles.

A further aspect of the invention relates to methods of using the compounds of Formula I of the present invention or compositions comprising the compounds of Formula I for the prophylaxis, amelioration and/or treatment of one or more condition(s)/disease(s)/disorder(s) of the central and/or peripheral nervous system, which comprises administering to a subject in need thereof the compounds of Formula I or compositions comprising a pharmaceutically effective amount of the compounds of Formula I.

Another aspect of the present invention is the use of a compound of Formula I for the manufacture of a medicament for the prophylaxis, amelioration and/or treatment of one or more condition(s)/disease(s)/disorder(s) of the central and/or peripheral nervous system, in a subject in need thereof preferably a mammal including a human.

The present invention also encompasses prodrugs and active metabolites of the compounds of the Formula I.

Other aspects of the invention will be set forth in the description which follows, and in part will be apparent from the description, or may be learnt by the practice of the invention.

DETAILED DESCRIPTION OF THE INVENTION

The present invention relates to the novel compounds of the Formula I,

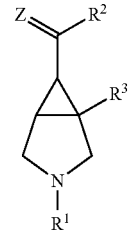

Formula I their pharmaceutically acceptable derivatives, tautomeric forms, isomers, polymorphs, prodrugs, metabolites, salts or solvates thereof, wherein:

$R^1$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl or heteroaryl; each of which may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO₂R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO₂, —OCSNR$^a$R$^b$, —SR$^a$, —S(O)R$^a$, —S(O)₂R$^a$, —SO₂NR$^a$R$^b$, —CR$^a$(=NOR$^b$), —CR$^a$(=NCOOR$^b$), —CR$^a$(=NSOR$^b$), —CR$^a$(=NSO₂R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$;

with the proviso that when $R^1$ is heterocyclyl, aryl or heteroaryl, then the said heterocyclyl, aryl or heteroaryl cannot be substituted with heterocyclyl;

$R^2$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl or heteroaryl; each of which may be optionally substituted at any available position by one or more substituents selected from but not limited to $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$;

R$^3$ represents —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl or heteroaryl; each of which may be optionally substituted at any available position by one or more substituents selected from but not limited to C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$;

provided that
(a) atleast one of R$^2$ and R$^3$ is aryl or heteroaryl
(b) when R$^3$ is aryl or heteroaryl, then R$^3$ cannot be substituted by heterocyclyl;

Z represents either NOR$^4$ or NNR$^4$R$^5$;

R$^4$ and R$^5$ are independently selected from —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl or heteroaryl; each of which may be optionally substituted at any available position by one or more substituents selected from but not limited to C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$;
or
R$^4$ and R$^5$ are joined together to form a heterocyclyl;
with the proviso that when Z is NOR$^4$, and R$^4$ is C$_{1-12}$ alkyl, then R$^2$ cannot be heterocyclyl or heteroaryl;

R$^a$, R$^b$, R$^c$ and R$^d$ are independently selected from —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH) or —CH(=NCN); wherein alkyl, alkenyl, alkynyl, cycloalkyl, cycloalkenyl, cycloalkynyl, heterocyclyl, aryl and heteroaryl groups may be optionally substituted at any available position by one or more substituents selected from but not limited to C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH) or —CH(=NCN);
or
R$^a$ and R$^b$ are joined together to form a C$_{3-7}$ cycloalkyl, C$_{3-7}$ cycloalkenyl, C$_{6-8}$ cycloalkynyl, heterocyclyl, aryl or heteroaryl;
or
R$^b$ and R$^c$ are joined together to form a C$_{3-7}$ cycloalkyl, C$_{3-7}$ cycloalkenyl, C$_{6-8}$ cycloalkynyl, heterocyclyl, aryl or heteroaryl;
or
R$^c$ and R$^d$ are joined together to form a C$_{3-7}$ cycloalkyl, C$_{3-7}$ cycloalkenyl, C$_{6-8}$ cycloalkynyl, heterocyclyl, aryl or heteroaryl.

One embodiment of the present invention provides compounds of Formula Ia, wherein

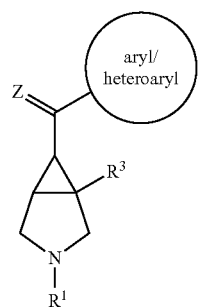

Formula Ia the said aryl or heteroaryl is unsubstituted or substituted, at any available position, with one or more substituents preferably selected from —F, —Cl, —Br, —I, —OH, —OR$^a$ and C$_{1-12}$ alkyl; R$^1$, R$^3$ and Z are as defined herein; their pharmaceutically acceptable derivatives, tautomeric forms, isomers, polymorphs, prodrugs, metabolites, salts or solvates thereof.

Another embodiment of the present invention provides compounds of Formula Ib, wherein

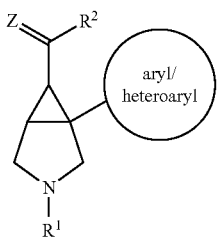

Formula Ib the said aryl or heteroaryl is unsubstituted or substituted, at any available position, with one or more substituents preferably selected from —F, —Cl, —Br, —I, —OH, —OR$^a$ and C$_{1-12}$ alkyl; R$^1$, R$^2$ and Z are as defined herein; their pharmaceutically acceptable derivatives, tautomeric forms, isomers, polymorphs, prodrugs, metabolites, salts or solvates thereof.

In another embodiment of the compounds of the present invention, it is preferred that R$^2$ and R$^3$ are independently selected from —H, C$_{1-12}$ alkyl, C$_{2-12}$ alkenyl, C$_{2-12}$ alkynyl, C$_{3-7}$ cycloalkyl, heterocyclyl, aryl and heteroaryl, each of which is unsubstituted or substituted, at any available position, with one or more substituents preferably selected from —F, —Cl, —Br, —I, —OH, —OR$^a$, C$_{1-12}$ alkyl, C$_{3-7}$ cycloalkyl, aryl and heteroaryl.

In a further embodiment of the compounds of the present invention, it is more preferred that R$^2$ and R$^3$ are independently selected from —H,

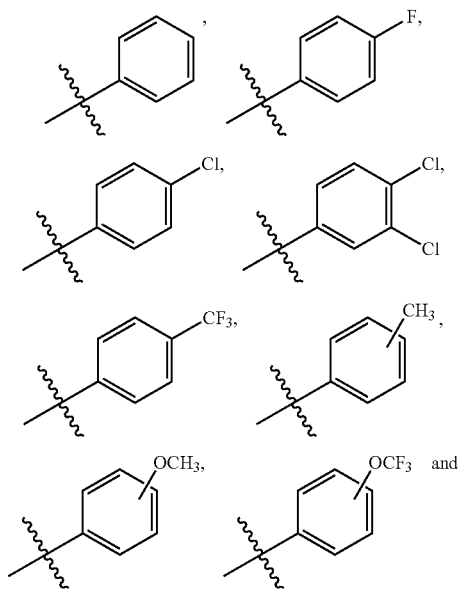

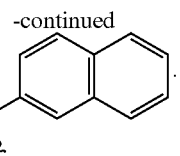

In another embodiment of the compounds of the present invention, it is preferred that R$^1$ is selected from —H, C$_{1-12}$ alkyl, C$_{2-12}$ alkenyl, C$_{2-12}$ alkynyl and C$_{3-7}$ cycloalkyl, each of which is unsubstituted or substituted, at any available position, with one or more substituents preferably selected from —F, —Cl, —Br, —I, —OH, C$_{3-7}$ cycloalkyl and —OR$^a$.

In a further embodiment of the compounds of the present invention, it is more preferred that R$^1$ is —H or C$_{1-12}$ alkyl.

In another embodiment of the compounds of the present invention, it is preferred that Z is NOR$^4$.

In still another embodiment of the compounds of the present invention, it is preferred that R$^4$ is selected from —H, C$_{1-12}$ alkyl, C$_{2-12}$ alkenyl, C$_{2-12}$ alkynyl, C$_{3-7}$ cycloalkyl, heterocyclyl, aryl and heteroaryl, each of which is unsubstituted or substituted, at any available position, with one or more substituents preferably selected from —F, —Cl, —Br, —I, C$_{3-7}$ cycloalkyl, heterocyclyl, aryl, heteroaryl, —OH, —OR$^a$ and —NR$^a$R$^b$; with the proviso that when R$^4$ is C$_{1-12}$ alkyl, then R$^2$ cannot be heterocyclyl or heteroaryl.

In a further embodiment of the compounds of the present invention, it is more preferred that R$^4$ is selected from —H, —CH$_3$, —C$_2$H$_5$, —CH$_2$—CH=CH$_2$, —C$_6$H$_5$, —CH$_2$—C$_6$H$_5$, —(CH$_2$)$_2$—OCH$_3$, —(CH$_2$)$_2$—NH$_2$,

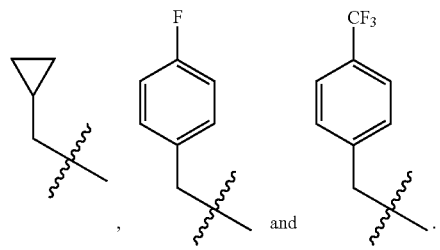 [SMILES: *CC1CC1 ; *Cc1ccc(F)cc1 ; *Cc1ccc(C(F)(F)F)cc1]

DEFINITIONS

Relative to the above description of the compounds of the present invention, the following definitions apply:

The term "alkyl" as used herein alone or as part of another group refers to a straight or branched chain aliphatic hydrocarbon chain, having from 1 to 12 carbon atoms. Examples of alkyl include, but are not limited to methyl, ethyl, n-propyl, isopropyl, n-butyl, n-pentyl, t-butyl and the like. Alkyl groups may further be substituted with one or more suitable substituents.

The term "alkenyl" as used herein alone or as part of another group refers to a straight or branched chain aliphatic hydrocarbon group containing at least one carbon-carbon double bond, having from 2 to 12 carbon atoms. Examples of alkenyl include, but are not limited to ethenyl, 1-propenyl, 2-propenyl, iso-propenyl, 1-butenyl, 2-butenyl, and the like. Alkenyl groups may further be substituted with one or more suitable substituents.

The term "alkynyl" as used herein alone or as part of another group refers to a straight or branched chain aliphatic hydrocarbon group containing at least one carbon-carbon triple bond, having from 2 to 12 carbon atoms. Examples of alkynyl include, but are not limited to ethynyl, propynyl, and butynyl. Alkynyl groups may further be substituted with one or more suitable substituents.

The term "cycloalkyl" refers to cyclic alkyl groups constituting of 3 to 20 carbon atoms having a single cyclic ring or multiple condensed rings, for example, fused or spiro systems, unless otherwise constrained by the definition. Such cycloalkyl groups include, by way of example, single ring structures, for example, cyclopropyl, cyclobutyl, cyclopentyl, cyclohexyl, cyclooctyl, and the like, or multiple ring structures, for example, adamantyl, and bicyclo[2.2.1]heptane, or cyclic alkyl groups to which is fused an aryl group, heteroaryl group, heterocyclyl group or another cycloalkyl group, for example, indane and the like. Cycloalkyl groups may further be substituted with one or more suitable substituents.

The term "cycloalkenyl" refers to a cycloalkyl group as defined above which may optionally contain one or more double bonds.

The term "cycloalkynyl" refers to a cycloalkyl group as defined above which may optionally contain one or more triple bonds.

The term "aryl" herein refers to a mono- or poly-carbocyclic aromatic group constituting of 5 to 15 carbon atoms, for example phenyl or naphthyl ring and the like optionally substituted with one or more suitable substituents. The aryl group may optionally be fused with cycloalkyl group, heteroaryl group, heterocyclyl group or another aryl group. The fused group may be further substituted with one or more suitable substituents.

The term "heteroaryl" unless and otherwise specified refers to an aromatic monocyclic or polycyclic ring structure constituting of 5 to 15 carbon atoms, containing one or more heteroatoms independently selected from N, O, S or P. The nitrogen, sulphur and phosphorus heteroatoms may optionally be oxidized. The nitrogen atoms may optionally be quaternerized. "Heteroaryl" also includes, but is not limited to, bicyclic or tricyclic rings, wherein the heteroaryl ring is fused to one or two rings independently selected from an aryl ring, a cycloalkyl ring, a cycloalkenyl ring, a heterocyclyl ring and another monocyclic heteroaryl ring. Examples of heteroaryl groups include, but are not limited to, oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, benzoxazolyl, imidazo[1,2-a]pyrimidine, imidazo[1,2-a]pyrazine, tetrahydroquinoline and the like. The heteroaryl group may be further substituted at any available position with one or more suitable substituents.

The term "heterocyclyl" unless otherwise specified refers to a non-aromatic monocyclic or polycyclic cycloalkyl group, fully or partially unsaturated, constituting of 5 to 15 carbon atoms, with one or more heteroatom(s) independently selected from N, O, S or P. The nitrogen, sulphur and phosphorus heteroatoms may optionally be oxidized. The nitrogen atoms may optionally be quaternerized. The heterocyclyl group may be further substituted at any available position with one or more suitable substituents. Examples of heterocyclyl groups include but are not limited to, morpholinyl, oxazolidinyl, tetrahydrofuranyl, dihydrofuranyl, dihydropyridinyl, dihydroisooxazolyl, dihydrobenzofuryl, azabicyclohexyl, dihydroindonyl, piperidinyl or piperazinyl.

"Halogen" refers to F, Cl, Br or I.

"Hydroxy" or "hydroxyl" refers to the group —OH.

The term "oxo" refers to carbonyl group represented as >C=O.

In all the above definitions, nitrogen, sulphur and phosphorus heteroatom can optionally be quaternerized or oxidized wherever permissible.

Examples of suitable substituents groups include but are not limited to, alkyl, alkenyl, alkynyl, aryl, cycloalkyl, cycloalkenyl, cycloalkynyl, heterocyclyl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN) and the like.

Comprises/comprising and grammatical variations thereof when used in the specification are to be taken to specify the presence of stated features, integers, steps, components or groups thereof, but do not preclude the presence or addition of one or more other features, integers, steps, components or groups thereof.

The term "Protecting Group" or "PG" refers to a group which is in a modified form to preclude undesired side reactions at the protected site. The term protecting group, unless otherwise specified, may be used with groups, for example, hydroxyl, amino, carboxyl and examples of such groups are found in T. W. Greene. et al. "*Protecting Groups in Organic Synthesis,*" 3$^{rd}$ Ed, Wiley, New York, which is incorporated herein by reference. The species of the carboxylic protecting groups, amino protecting groups or hydroxyl protecting groups employed are not critical, as long as the derivatised moieties/moiety is/are stable to conditions of subsequent reactions and can be removed without disrupting the remainder of the molecule. Examples of suitable hydroxyl and amino protecting groups include but are not limited to trimethylsilyl, triethylsilyl, o-nitrobenzyloxycarbonyl, p-nitrobenzyloxycarbonyl, t-butyldiphenylsilyl, t-butyldimethylsilyl, acetyl, trifluoroacetyl, benzyloxycarbonyl (CBz), t-butoxycarbonyl (Boc), 9-fluorenylmethylenoxycarbonyl (Fmoc), 2,2,2-trichloroethyloxycarbonyl, allyloxycarbonyl and the like. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl, t-butyl and the like.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity, weight, physical condition and responsiveness of the mammal to be treated, among other factors.

A "pharmaceutically acceptable salt" refers to salts prepared from pharmaceutically acceptable non-toxic bases or acids including inorganic or organic bases and inorganic or organic acids.

Asymmetric centres may exist in the compounds of the present invention. The compounds of Formula I may have one or more stereogenic centres and so can exhibit optical isomerism. All such isomers including enantiomers, diastereomers, and epimers are included within the scope of this invention. Furthermore, the invention includes such compounds as single isomers (R and/or S) and as mixtures, including racemates. If desired, racemic mixtures of the compounds may be separated so that the individual enantiomers are isolated. The separation may be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Starting materials of particular stereochemistry may either be commercially available or may be made by the methods described herein and resolved by techniques well known in the art. The independent syntheses of these diastereomers or their chromatographic separations may be achieved as known in the art by appropriate modifications.

Certain compounds according to Formula I, can also exist as tautomers, which have different points of attachment of hydrogen accompanied by one or more double bond shifts. These tautomers, either separately or as mixtures, are also considered to be within the scope of the invention.

The present invention also encompasses geometrical isomers of compounds of Formula I and the mixtures thereof. The geometrical isomers may exist in E or Z; syn or anti configurations. These geometrical isomers, either separately or as mixtures, are also considered to be within the scope of the invention.

Particularly useful examples of the present invention include but are not limited to the compounds selected from Table I, including their pharmaceutically acceptable derivatives, tautomeric forms, isomers, polymorphs, prodrugs, metabolites, salts or solvates thereof:

TABLE I

| Compound No | Structure |
| --- | --- |
| 1 | |
| 2 | |
| 3 | |
| 4 | 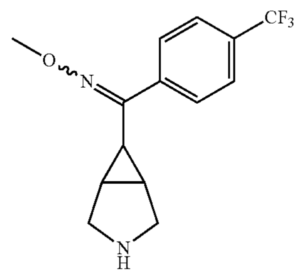 [SMILES: CON=C(c1ccc(C(F)(F)F)cc1)C1C2CNCC21] |
| 5 | 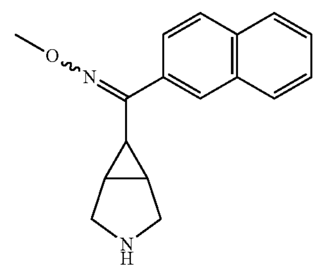 [SMILES: CON=C(c1ccc2ccccc2c1)C1C2CNCC21] |
| 6 | 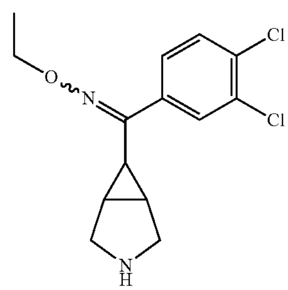 [SMILES: CCON=C(c1ccc(Cl)c(Cl)c1)C1C2CNCC21] |
| 7 | 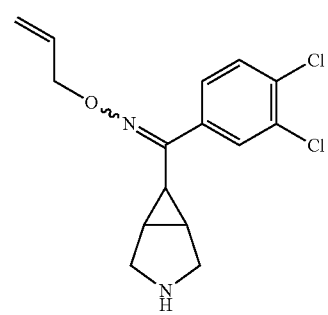 [SMILES: C=CCON=C(c1ccc(Cl)c(Cl)c1)C1C2CNCC21] |
| 8 | 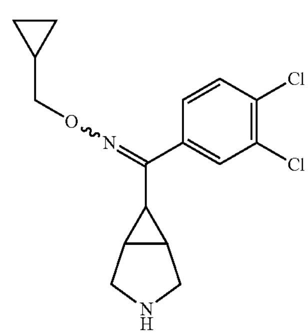 [SMILES: Clc1ccc(C(=NOCC2CC2)C2C3CNCC32)cc1Cl] |

TABLE I-continued

| Compound No | Structure |
|---|---|
| 9 | 3,4-dichlorophenyl, phenoxy-imine, 3-azabicyclo[3.1.0]hexane |
| 10 | 3,4-dichlorophenyl, benzyloxy-imine, 3-azabicyclo[3.1.0]hexane |
| 11 | 3,4-dichlorophenyl, (4-fluorobenzyl)oxy-imine, 3-azabicyclo[3.1.0]hexane |
| 12 | 3,4-dichlorophenyl, (4-trifluoromethylbenzyl)oxy-imine, 3-azabicyclo[3.1.0]hexane |

TABLE I-continued

| Compound No | Structure |
|---|---|
| 13 | phenyl-substituted 3-azabicyclo[3.1.0]hexane with methoxyimine |
| 14 | (4-fluorophenyl)-substituted 3-azabicyclo[3.1.0]hexane with methoxyimine |
| 15 | (4-chlorophenyl)-substituted 3-azabicyclo[3.1.0]hexane with methoxyimine |
| 16 | (3,4-dichlorophenyl)-substituted 3-azabicyclo[3.1.0]hexane with methoxyimine |
| 17 | (3,4-dichlorophenyl)-substituted 3-azabicyclo[3.1.0]hexane with ethoxyimine |

TABLE I-continued

| Compound No | Structure |
|---|---|
| 18 | (structure: benzyl-O-N=CH-cyclopropane fused pyrrolidine with 3,4-dichlorophenyl) |
| 19 | (structure: 4-fluorobenzyl-O-N=CH-cyclopropane fused pyrrolidine with 3,4-dichlorophenyl) |

Compounds of Formula I can be prepared starting from compounds of Formula II. Compounds of Formula II can be prepared according to various procedures described in literature, for example, when $R^3$=H, $R^2$=Ar, the compounds can be prepared according to the procedure given in *Synlett*, 1996, 1097-1099 and when $R^3$=Ar, $R^2$=H, the synthetic scheme given in WO 2009141412 and WO 2008074716 is used.

One convenient route for the conversion of compounds of Formula II to compounds of Formula I (when Z=NOR$^4$) is outlined in Scheme 1. The compounds of Formula II (when $R^2$ is any group other than hydrogen and PG=protecting group of nitrogen), are converted to compounds of Formula III by the addition of various Grignard reagents $R^2$MgX in the presence of solvents like THF, diethyl ether, toluene and the like, at temperatures ranging from 0° C. to −78° C. The protecting group on nitrogen can be selected from but not limited to a carbamate group (e.g, methyl carbamate, ethyl carbamate, benzyl carbamate, 9-fluorenylmethyl carbamate, 2,2,2-trichloroethyl carbamate, 2-phenylethyl carbamate, allyl carbamate, benzyl carbamate and the like), urea type derivatives (e.g., N'-p-toluenesulfonylaminocarbonyl and the like), amides (e.g., N-formyl, N-acetyl, N-trifluoroacetyl, N-picolinyl, N-benzoyl and the like), alkyl and aryl amines (e.g., N-methyl, N-allyl, N-acetoxypropyl, N-benzyl and the like) or enamine derivatives (e.g., N-2,7,-dichloro-9-fluorenylmethylene and the like). Compounds of Formula III are then converted to compounds of Formula IV by known methods of oxidation of alcohols such as Swern oxidation (oxalyl chloride-dimethylsulfoxide-triethylamine), Jones oxidation or by using reagents such as TCCA, TEMPO, PCC, PDC etc. in solvents like DCM, DCE and the like. Compounds of Formula IV are further condensed with appropriately substituted, hydroxyl amine salts, by methods known in literature (*J. Med. Chem.* 1999, 42, 742-750; *J. Med. Chem.* 2002, 45, 3143-3160), resulting in the formation of compounds of Formula V. Compounds of Formula VI can easily be prepared from compounds of Formula V by deprotecting the amine protecting group, using standard deprotecting reagents. The resulting compounds may be in the form of free amine or salt depending upon the nature of the protecting groups and the corresponding deprotecting reagents. Examples of reagents used for deprotecting the amine protecting moiety include but are not limited to use of acidic conditions (trifluoroacetic acid, hydrochloric acid, phosphoric acid, p-toluenesulphonic acid and the like) or basic conditions (piperidine, $K_2CO_3$/MeOH and the like). In case, the deprotection results in the formation of salt, the corresponding amine can easily be obtained by treating the salt with an appropriate base such as triethylamine, diethylisopropylamine, sodium bicarbonate, sodium hydroxide or the like. Compounds of Formula VI can then be alkylated by using various alkyl halides under various basic conditions using solvents like DCM, THF, dioxane, acetonitrile and so on by known methods described in literature to give compounds of Formula I, wherein $R^1$, $R^2$, $R^3$ and $R^4$ are as defined herein.

Scheme 1

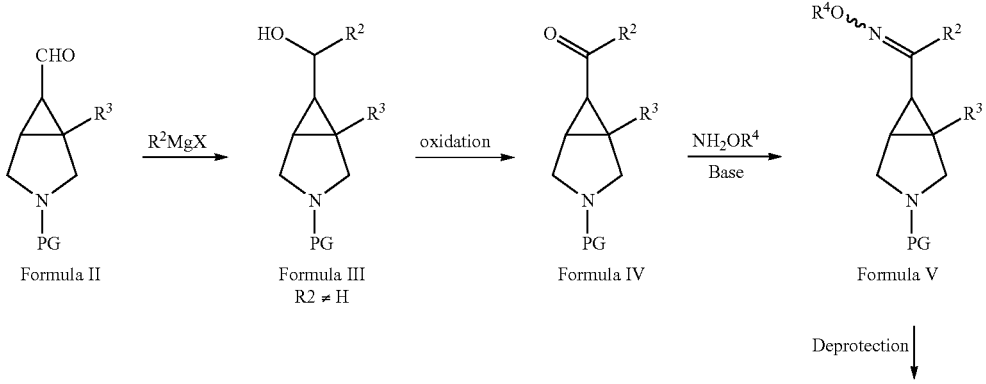

Deprotection

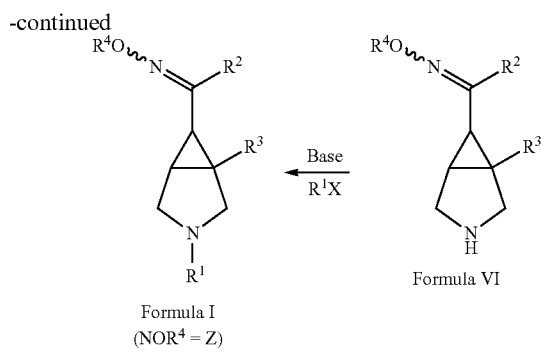

Formula I
(NOR⁴ = Z)

Formula VI

Alternatively, as shown in Scheme 2, the compounds of Formula IV are converted to compounds of Formula V by reacting them with commercially available hydroxyl amine hydrochloride by known methods in literature (*J. Med. Chem.* 1999, 42, 742-750; *J. Med. Chem.* 2002, 45, 3143-3160) to give the compounds of Formula IVa, which are further alkylated with alkyl halides using bases like sodium hydride, sodium tert-butoxide, potassium tert-butoxide, potassium hexamethyldisilazane, sodium hexamethyldisilazane, lithium hexamethyldisilazane and so on using solvents like DMF, THF by known methods in literature (*J. Med. Chem.* 1999, 42, 743; *J. Med. Chem.* 2002, 45, 3145) to give compounds of Formula V.

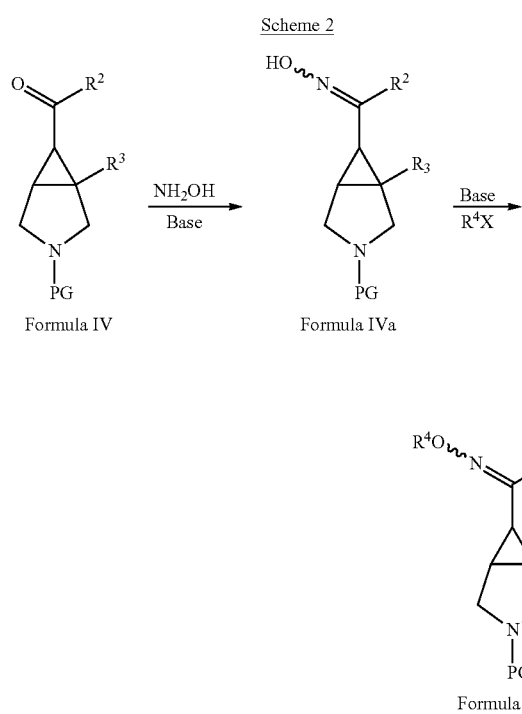

Scheme 2

Formula IV — Formula IVa — Formula V

The commercially non available hydroxyl amines of formula $NH_2OR^4$ can also be prepared by following Scheme 3, using N-hydroxyphthalimide, alkyl halides and various bases like sodium hydride, potassium carbonate, LDA, potassium tert-butoxide, sodium tert-butoxide, LiHMDS. These type of transformations can be performed by methods known as described in U.S. Pat. No. 5,120,849 and *Chem. Pharm. Bull,* 2003, 51, 138-151.

Scheme 3

For the preparation of the compounds of Formula I where $R^2$=H, the procedure described in Scheme 4 is used. Compounds of Formula II are reacted with appropriately substituted hydroxyl amine salts by known methods in literature (*J. Med. Chem.* 1999, 42, 742-750; *J. Med. Chem.* 2002, 45, 3143-3160) resulting in the formation of compounds of Formula VII. Compounds of Formula VIII can easily be prepared from compounds of Formula VII by deprotecting the amine protecting group, using standard deprotecting reagents. Compounds of Formula VIII are subsequently alkylated with alkyl halides using bases like sodium hydride, sodium tert-butoxide, potassium tert-butoxide, potassium hexamethyldisilazane, sodium hexamethyldisilazane, lithium hexamethyldisilazane and so on using solvents like DMF, THF by known methods in literature (*J. Med. Chem.* 1999, 42, 743; *J. Med. Chem.* 2002, 45, 3145) to give compounds of Formula I.

Scheme 4

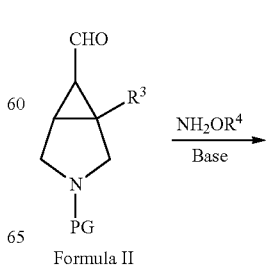

Formula II

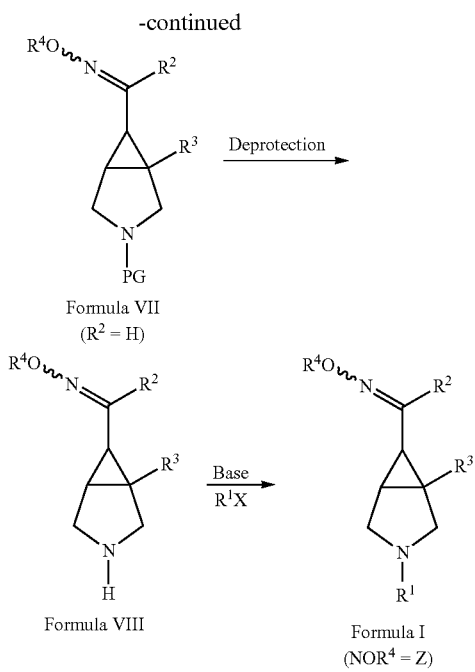

It is understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. The salts may be prepared during the final isolation and purification of the compounds or separately by making basic or acidic addition salts. Representative salts of basic compounds of the present invention can be prepared by reacting free base form of the compound with a suitable acid. These salts include, but are not limited to acetate, trifluoroacetate, adipate, citrate, aspartate, benzoate, benzenesulphonate, bisulfate, besylate, butyrate, camphorsulphonate, difluconae, hemisulfate, heptanoate, formate, fumarate, lactate, maleate, methanesulfonate, naphthylsulfonate, nicotinate, oxalate, picrate, pivalate, succinate, tartrate, tirchloracetat, glutamate, p-toluenesulphonate, hydrochloric, hydrobromic, sulphuric, phosphoric and the like. Representative salts of acidic compounds of the present invention can be prepared by reacting free acid form of the compound with a suitable base. The resulting salts include, but are not limited to ammonium, calcium, magnesium, potassium, sodium salts, salts of primary, secondary and tertiary amines, substituted amines including naturally occurring ones e.g., arginine, betaine, caffeine, choline, glucamine, glucosamine, histidine, lysine, morpholine, piperazine, piperidine, purine, triethylamine and the like. Compounds of the present invention that contain a carboxylic acid (—COOH) or alcohol group, their pharmaceutically acceptable esters of carboxylic acids such as methyl, ethyl and the like, or acyl derivatives of alcohols such as acetate and the like, can be employed. Compounds of the present invention that comprise basic nitrogen atom may be quaternized with alkyl halides, alkyl sulfates and the like. Such salts permit the preparation of both water soluble and oil soluble compounds of the present invention. It should be recognized that the free base or free acid forms will typically differ from their respective salt forms somewhat in physical properties such as solubility in polar solvents, but otherwise the salts are equivalent to their respective free forms for the purpose of the invention.

The "pharmaceutically acceptable solvates" refer to solvates with water (i.e., hydrates) or pharmaceutically acceptable solvents, for example, ethanol and the like.

The invention also encompasses "prodrugs" of the compounds of the present invention, upon in-vivo administration undergo chemical conversion by metabolic processes before becoming active pharmacological substances. In general such prodrugs will be functional derivatives of a compound of the invention which are readily convertible in vivo into the compound of the invention. Conventional procedures for the selection and preparation of suitable prodrug derivatives are described, for example, in "Targeted prodrug design to optimize drug delivery", *AAPS PharmaSci* 2000, 2(1), E6. In certain cases, the prodrug itself can also have biological activity in the disease area.

Preferably, the invention encompasses Nitrogen prodrugs (N-prodrugs) and Oxygen prodrugs (O-prodrugs) of the compounds of the present invention which upon in-vivo administration undergo chemical conversion by metabolic processes before becoming active pharmacological substances. In general such N-prodrugs can be represented by N-Alkyl (N-methyl, N-ethyl, N-benzyl and the like), N-Acyl (N-acetyl, N-propionyl, N-benzoyl, N-methoxycarbonyl, N-ethoxycarbonyl, N-tert Butyloxycarbonyl and the like), N-Acyloxyalkyl (N-acetyloxymethyl and the like), N-hydroxyalkyl (N-hydroxymethyl and the like), Schiff bases and the like. O-prodrugs can be represented in general by O-alkyl ethers (methyl, ethyl, substituted alkyl ethers like methoxymethyl, ethoxyethyl and the like), O-allyl ethers, O-benzyl ethers, O-substituted benzyl ethers, O-esters (e.g., formate, benzoyl, acetate, benzoate and the like), or carbonates (e.g., methyl, methoxymethyl and the like) and the like.

The invention also encompasses active "metabolites" of the compound of the present invention. When a metabolite of a drug produces a therapeutic effect it is considered an active metabolite.

Various "polymorphs" of a compound of general Formula I forming part of this invention may be prepared by crystallization of a compound of Formula I under different conditions. For example, by using different solvents commonly used or their mixtures for recrystallization; crystallizations at different temperatures; various modes of cooling, ranging from very fast to very slow cooling during crystallizations, heating or melting the compound followed by gradual or fast cooling may also obtain polymorphs. The presence of polymorphs may be determined by solid probe NMR spectroscopy, IR spectroscopy, differential scanning calorimetry, powder X-ray diffraction or such other techniques.

The present invention also provides pharmaceutical compositions, comprising compounds of general Formula I or their pharmaceutically acceptable analogs, tautomeric forms, isomers, polymorphs, prodrugs, metabolites, salts or solvates thereof together with one or more pharmaceutically acceptable carriers comprising excipients and auxiliaries, which facilitate processing of the active compound into preparations, which can be used pharmaceutically. The pharmaceutical compositions may be in the forms normally employed, such as tablets, capsules, powders, syrups, solutions, suspensions, emulsions, pills, granules, suppositories, pellets, depot formulations and the like, may contain flavourants, sweeteners etc in suitable solid or liquid carriers or diluents, or in suitable sterile media to form injectable solutions or suspensions. Such compositions typically contain from 0.1 to 99.9% by weight of active compound, the remainder of the composition being pharmaceutically acceptable carriers, diluents or solvents.

The pharmaceutical compositions of the present invention can be manufactured by processes well known in the art, for example, by means of conventional mixing, dissolving, dry granulation, wet granulation, dragee-making, levigating, emulsifying, encapsulating, entrapping, lyophilizing processes or spray drying. The compounds or the pharmaceutical compositions comprising such compounds of the present invention may be administered in the form of any pharmaceutical formulation. The pharmaceutical formulation will depend upon the nature of the active compound and its route of administration. Any route of administration may be used, for example oral, buccal, pulmonary, topical, parenteral (including subcutaneous, intramuscular and intravenous), transdermal, ocular (ophthalmic), by inhalation, intranasal, transmucosal, implant or rectal administration. Preferably the compounds of the present invention are administered orally, parenterally or topically.

In an embodiment, the amount of the novel compounds having the Formula I according to the present invention to be incorporated into the pharmaceutical compositions of the present invention can vary over a wide range depending on known factors such as, for example, the disorder to be treated, the severity of the disorder, the patient's body weight, the dosage form, the chosen route of administration and the number of administration per day. Typically, the amount of the compound of Formula I in the pharmaceutical compositions of the present invention will range from approximately 0.01 mg to about 5000 mg. In an embodiment, the daily dose of composition comprising the novel compounds having the Formula I is in the range of about 0.01 mg/kg to about 100 mg/kg based on the body weight of the subject in need thereof which may be administered as a single or multiple doses.

In one embodiment compounds of the present invention are useful in the prophylaxis, amelioration and/or treatment of one or more condition(s)/disease(s)/disorder(s), in a subject in need thereof preferably a mammal including a human.

In another embodiment compounds of the present invention are useful in the prophylaxis, amelioration and/or treatment of one or more condition(s)/disease(s)/disorder(s) of the central and/or peripheral nervous system, in a subject in need thereof preferably a mammal including a human.

In further embodiment compounds of the present invention are useful in the prophylaxis, amelioration and/or treatment of one or more condition(s)/disease(s)/disorder(s) of the central and/or peripheral nervous system that are responsive to modulation of neurological and/or psychiatric targets (GPCR and/or non-GPCR), in a subject in need thereof preferably a mammal including a human.

In still further embodiment compounds of the present invention are useful in the prophylaxis, amelioration and/or treatment of one or more condition(s)/disease(s)/disorder(s) of the central and/or peripheral nervous system that are responsive to modulation of biogenic amines and/or their receptors, in particular one or more, or any combination of serotonin, norepinephrine or dopamine, in a subject in need thereof preferably a mammal including a human.

The condition(s)/disease(s)/disorder(s) of the central and/or peripheral nervous system that may be treated, controlled, or in some cases prevented, by treatment with compounds of the present invention include, but are not limited to, for example, depression, psychotic disorders, mood disorders, bipolar disorders, personality disorders, eating disorders, aggressive behavior, schizophrenia, inflammatory bowel disorders, irritable bowel syndrome, pain, chronic neuropathic pain, addiction disorders including cocaine abuse, urinary incontinence, dementia, Alzheimer's memory loss, Parkinsonism, stroke, anxiety, attention-deficit disorder, social phobia, pathological crying and/or laughing, obsessive compulsive disorder, substance (like nicotine, alcohol and opium) abuse and withdrawal (substance related disorder), cognitive disorders, fibromyalgia, Interstitial cystitis, Nocturnal enuresis, Ciguatera poisoning, Body dysmorphic disorder, Lichen simplex chronicus, chronic hiccups and sleep disorders. Included among these disorders are disorders related to depression, such as pseudodementia, migraine pain or headache, bulimia, obesity, pre-menstrual syndrome or late luteal phase syndrome, tobacco abuse, smoking, panic disorder, memory loss, dementia of ageing, acquired immunodeficiency syndrome dementia complex, memory dysfunction in ageing, anti-attention deficit hyperactivity disorder (ADHD), chronic fatigue syndrome, premature ejaculation, erectile difficulty, anorexia nervosa, narcolepsy, Gilles de la Tourettes disease, presenile dementia, senile dementia, cognition impairment, sexual dysfunctions, disorders of sleep or autism, mutism or trichotillomania.

All of the various forms and sub-forms of the disorders mentioned herein are contemplated as part of the present invention.

The neurological and/or psychiatric targets (GPCR and/or non-GPCR) which may be modulated with compounds of the present invention for treatment, control, or in some cases prevention of the aforementioned disorders include, but are not limited to, for example biogenic amine transport, HPA axis, hippocampus dysfunction, neurotrophic mechanism of modulating neuroplasticity; Aldosterone; APJ; Calcitonin, Calcitonin Gene-Related Peptide CGRP1; Adrenomedullin AM2; Acetycholine (muscarinic) $M_1$, $M_2$, $M_4$, $M_5$ or Glutamatergic receptors namely, ionotropic receptors (NMDA, AMPA, and kainate receptors) and metabotropic receptors (G-protein coupled receptors); Adenosine $A_1$; Adrenoceptor $\alpha_{1B}$, $\alpha_{2A}$, $\beta_{1, 2, 3}$; Bombesin BB2; Bradykinin B2; Cannabinoid CB1; Chemokine CCR2B, CXCR3; Cholecystokinin CCK1, CCK2; Dopamine D1, D2L, D5; Endothelin ETB, Endothelin ETA; $GABA_A$; G Protein-Coupled Receptor GPR8, GPR5, GPR103; g-Hydroxybutyric Acid (GHB) Receptor; Galanin GAL1, GAL2; Glucagon GLP-1, Secretin receptor; vanilloid; Atrial Natriuretic Factor (ANF); Tumor Necrosis Factor (TNF), non selective; Gonadotropin-Releasing Hormone; Inositol Triphosphate IP3; Interleukin IL-2; Choline transporter; Vascular Endothelial Growth Factor (VEGF); Leukotriene, BLT (LTB4), Cysteinyl CysLT1,2; Glutamate(metabotropic) mGlu, NMDA, AMPA, Kainate; Motilin; Glycoprotein hormone TSH; Histamine H1, H2, H3; Lysophospholipid S1P1, S1P5, LPA1; CYP450 2C8; Insulin; Growth Hormone Secretagogue (GHS, Ghrelin); Imidazole 12 central, peripheral; Melanocortin MC3, MC4, MC5; Neuropeptide Y2; NPY acting via Y1 receptors; Neuromedin U NMU2; Neurotensin NTR1; N-formylpeptide FPR1, FPRL1; Nicotinic acid GPR109A; Estrogen ER; Progesterone, Progesterone PR-B; Melatonin MT1 and MT2 receptor; Purinergic P2x; Orphanin ORL1; Opioid Delta, Mu, NOP/ORL1, OX1; P2Y P2RY1; Potassium Channel HERG, KA, SKCa; Platelet Activating Factor (PAF); Prolactin-releasing peptide; Urotensin II; Prostanoid EP1, EP2; Pituitary Adenylate Cyclase-Activating Polypeptide-Type I (PAC1); Rolipram; Serotonin $5\text{-}HT_{1A}$, $5\text{-}HT_{2C}$, $5\text{-}HT_{2A}$, $5\text{-}HT_3$, $5\text{-}HT_6$, $5\text{-}HT_7$; Somatostatin SST2, SST4; Sigma 1,2, Sigma non-selective; Sodium Channel, Site 2; Tachykinin/neurokinin NK1, NK2, NK3; VIP/PACAP PAC1 long isoform, VPAC1, VPAC2;

Vitamin D3; Adrenoceptor alpha2A; Corticotropin releasing factor CRF1, CRF2; Lysophospholipid LPA1; Melanin-concentrating hormone MCHR1; Opiods (Delta, mu, kappa & NOP/ORL1); Orexin OX1, OX2; Vasopressin V(1b); Sigma $\delta_1$; Melatonin MT1, MT2; BDNF, TrkB; Phospodiesterase; Beta adrenoceptor β-1,2,3; Glucorticoid receptor antagonists; Calcium channels, glycine receptors; MAO; Nitric Oxide Synthase; and various other GPCRs targeting neurological and psychiatric disorders.

The biogenic amines are a group of naturally occurring biologically active compounds, most of which act as neurotransmitters. The biogenic amines include serotonin, norepinephrine and dopamine and may include other biogenic amines which can act as neurotransmitters in central and/or peripheral nervous system.

In still another embodiment of the present invention is provided use of the dosage form compositions comprising the novel compounds of Formula I for the treatment of one or more condition(s)/disease(s)/disorder(s), which comprises administrating to a subject in need thereof a pharmaceutically effective amount of the composition.

In another embodiment of the present invention is provided use of the dosage form compositions comprising the novel compounds of Formula I for the treatment of one or more condition(s)/disease(s)/disorder(s) of the central and/or peripheral nervous system, which comprises administrating to a subject in need thereof a pharmaceutically effective amount of the composition.

A further embodiment of the present invention provides use of the dosage form compositions comprising the novel compounds of Formula I for the treatment of one or more condition(s)/disease(s)/disorder(s) of the central and/or peripheral nervous system that are responsive to modulation of neurological and/or psychiatric targets (GPCR and/or non-GPCR), which comprises administrating to a subject in need thereof a pharmaceutically effective amount of the composition.

A still further embodiment of the present invention provides use of the dosage form compositions comprising the novel compounds of Formula I for the treatment of one or more condition(s)/disease(s)/disorder(s) of the central and/or peripheral nervous system that are responsive to modulation of biogenic amines and/or their receptors, in particular one or more, or any combination of serotonin, norepinephrine and dopamine, which comprises administrating to a subject in need thereof a pharmaceutically effective amount of the composition.

Another embodiment of the present invention is the use of a compound of Formula I for the manufacture of a medicament for the prophylaxis, amelioration and/or treatment of one or more condition(s)/disease(s)/disorder(s), in a subject in need thereof preferably a mammal including a human.

In still another embodiment of the present invention is the use of a compound of Formula I for the manufacture of a medicament for the prophylaxis, amelioration and/or treatment of one or more condition(s)/disease(s)/disorder(s) of the central and/or peripheral nervous system, in a subject in need thereof preferably a mammal including a human.

In another embodiment of the present invention is the use of a compound of Formula I for the manufacture of a medicament for the prophylaxis, amelioration and/or treatment of one or more condition(s)/disease(s)/disorder(s) of the central and/or peripheral nervous system that are responsive to modulation of neurological and/or psychiatric targets (GPCR and/or non-GPCR), in a subject in need thereof preferably a mammal including a human.

A further embodiment of the present invention is the use of a compound of Formula I for the manufacture of a medicament for the prophylaxis, amelioration and/or treatment of one or more condition(s)/disease(s)/disorder(s) of the central and/or peripheral nervous system that are responsive to modulation of biogenic amines and/or their receptors, in particular one or more, or any combination of serotonin, norepinephrine and dopamine, in a subject in need thereof preferably a mammal including a human.

An embodiment of the present invention relates to methods of using the compounds of Formula I of the present invention or compositions comprising the compounds of Formula I for the prophylaxis, amelioration and/or treatment of any one or more condition(s)/disease(s)/disorder(s), which comprises administering to a subject in need thereof the compounds of Formula I or compositions comprising a pharmaceutically effective amount of the compounds of Formula I.

Further an embodiment of the present invention relates to methods of using the compounds of Formula I of the present invention or compositions comprising the compounds of Formula I for the prophylaxis, amelioration and/or treatment of one or more condition(s)/disease(s)/disorder(s) of the central and/or peripheral nervous system, which comprises administering to a subject in need thereof the compounds of Formula I or compositions comprising a pharmaceutically effective amount of the compounds of Formula I.

Still another embodiment of the present invention relates to methods of using the compounds of Formula I of the present invention or compositions comprising the compounds of Formula I for the prophylaxis, amelioration and/or treatment of one or more condition(s)/disease(s)/disorder(s) of the central and/or peripheral nervous system, that are responsive to modulation of neurological and/or psychiatric targets (GPCR and/or non-GPCR), which comprises administering to a subject in need thereof the compounds of Formula I or compositions comprising a pharmaceutically effective amount of the compounds of Formula I.

A further embodiment of the present invention relates to methods of using the compounds of Formula I of the present invention or compositions comprising the compounds of Formula I for the prophylaxis, amelioration and/or treatment of one or more condition(s)/disease(s)/disorder(s) of the central and/or peripheral nervous system that are responsive to modulation of biogenic amines and/or their receptors, in particular one or more, or any combination of serotonin, norepinephrine and dopamine, which comprises administering to a subject in need thereof the compounds of Formula I or compositions comprising a pharmaceutically effective amount of the compounds of Formula I.

An embodiment of the present invention provides methods for the prophylaxis, amelioration and/or treatment of one or more one or more condition(s)/disease(s)/disorder(s), in a subject in need thereof preferably a mammal including a human, that comprises administering a therapeutically effective amount of compound of Formula I.

Another embodiment of the present invention further provides methods for the prophylaxis, amelioration and/or treatment of one or more one or more condition(s)/disease(s)/disorder(s) of the central and/or peripheral nervous system, in a subject in need thereof preferably a mammal including a human, that comprises administering a therapeutically effective amount of compound of Formula I.

A further embodiment of the present invention provides methods for the prophylaxis, amelioration and/or treatment of one or more one or more condition(s)/disease(s)/disorder(s) of the central and/or peripheral nervous system that are responsive to modulation of neurological and/or psychiatric targets (GPCR and/or non-GPCR), in a subject in need thereof preferably a mammal including a human, that comprises administering a therapeutically effective amount of compound of Formula I.

A still further embodiment of the present invention provides methods for the prophylaxis, amelioration and/or treatment of one or more one or more condition(s)/disease(s)/disorder(s) of the central and/or peripheral nervous system that are responsive to modulation of biogenic amines and/or their receptors, in particular one or more, or any combination of serotonin, norepinephrine and dopamine, in a subject in need thereof preferably a mammal including a human, that comprises administering a therapeutically effective amount of compound of Formula I.

In another embodiment, the novel compounds having the Formula I according to the present invention are particularly useful for the treatment of disease(s) or disorder(s) which are particularly acute in nature and which require a short term but mild to moderate treatment, or even some chronic conditions which favorably respond to or are alleviated by the novel compounds having the Formula I or compositions comprising them. The compositions comprising the novel compounds having the Formula I are useful prophylactically or therapeutically depending upon the condition intended to be prevented or treated respectively.

In another embodiment compounds of the present invention may be useful in the treatment of depression which includes, but is not limited to, Depression and mood disorders including Major Depressive Episode, Manic Episode, Mixed Episode and Hypomanic Episode; Depressive Disorders including Major Depressive Disorder, Dysthymic Disorder, Depressive Disorder not otherwise specified; Other Mood Disorders including Mood Disorder due to a general medical condition which includes the subtypes with depressive features, with major depressive-like episode, with manic features and mixed features, Substance-induced Mood Disorder (including the subtypes with depressive features, with manic features and with mixed features), dysthymia and mood disorders not otherwise specified; Bipolar Disorders including Bipolar I Disorder, Bipolar II Disorder (Recurrent Major Depressive Episodes with Hypomanic Episodes), Cylothymic disorder, and Bipolar Disorder not otherwise specified; Neuralgia (neuropathic pain) and fibromyalgia.

In an embodiment, compounds of the present invention may be useful as analgesics to relieve pain. For example they may be useful in the treatment of conditions which include but are not limited to chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain, sympathetically maintained pain myositis, pain associated with cancer and fibromyalgia; pain associated with migraine; pain associated with influenza or other viral infections, such as common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

In a further embodiment compounds of the present invention may be useful in the treatment of neuropathic pain which includes, but is not limited to, diabetic neuropathy, sciatica, non-specific lower back pain, multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. Neuropathic pain may be spontaneous shooting and lancinating pain; ongoing, burning pain; pain associated with normally non-painful sensations such as "pins and needles" (paraesthesias and dysesthesias), increased sensitivity to touch (hyperesthesia) and; pain associated with painful sensation following innocuous stimulation (dynamic, static or thermal allodynia), increased sensitivity to noxious stimuli (thermal, cold, mechanical hyperalgesia), continuing pain sensation after removal of stimulation (hyperpathia) or an absence of or deficit in selective sensory pathways (hypoalgesia).

In an embodiment compounds of the present invention may be useful in the treatment of anxiety which includes, but is not limited to, anxiety disorders including Panic Attack, Panic Disorder in Panic Disorder without Agoraphobia and panic disorder with Agoraphobia; Agoraphobia; Agoraphobia without history of panic disorder, specific phobia including the subtypes Animal Type, Natural Environment Type, blood-injection-injury type, situational type and other type; Social phobia (Social Anxiety Disorder), Obsessive-Compulsive Disorder, Personality disorders such as borderline personality disorder (BPD), attention-deficit hyperactivity disorder (ADHD) and personality disorder not otherwise specified; Posttraumatic stress disorder, acute stress disorder, generalized anxiety disorder, depression related anxiety, anxiety disorder due to a general medical condition, substance-induced anxiety disorder, Separation anxiety disorder, adjustment disorder with anxiety, and anxiety disorder not otherwise specified.

In a further embodiment compounds of the present invention may be useful in the treatment of substance related disorders which include, but are not limited to, substance-related disorders including substance use disorders such as Substance Dependence, Substance craving and substance abuse; substance-induced Disorders such as Substance Intoxication, Substance Withdrawal, substance-induced Delirium, substance-induced persisting dementia, substance-induced persisting amnestic disorder, substance-induced psychotic disorder, substance-induced mood disorder, substance-induced Mood disorder, substance-induced anxiety disorder, substance-induced sexual dysfunction, substance-induced sleep disorder and hallucinogen persisting perception disorder (Flashbacks); Alcohol-related disorders such as alcohol dependence, alcohol abuse, alcohol intoxication, alcohol withdrawal, alcohol intoxication delirium, alcohol withdrawal delirium, alcohol-induced persisting dementia, alcohol-induced persisting amnestic disorder, alcohol-induced psychotic disorder, alcohol-induced mood disorder, alcohol-induced anxiety disorder, alcohol-induced sexual dysfunction, alcohol-induced sleep disorder and alcohol related disorder not otherwise specified; Amphetamine (or Amphetamine like)-related disorder such as Amphetamine dependence, Amphetamine abuse, Amphetamine intoxication, Amphetamine withdrawal, Amphetamine intoxication delirium, Amphetamine-induced psychotic disorder, Amphetamine-induced mood disorder, Amphetamine-induced anxiety disorder, Amphetamine-induced sexual dysfunction, Amphetamine-induced sleep disorder and Amphetamine related disorder not otherwise specified; Caffeine related disorders such as caffeine intoxication, caffeine induced anxiety disorder, caffeine induced sleep disorder and caffeine related disorder not otherwise specified; Cannabis-related disorders such as cannabis dependence, cannabis abuse, cannabis intoxication, cannabis intoxication delirium, cannabis induced psychotic disorder, cannabis induced anxiety disorder and cannabis related disorder not otherwise specified; Cocaine-related disorders such as Cocaine dependence, Cocaine abuse, Cocaine intoxication, Cocaine withdrawal, Cocaine intoxication delirium, Cocaine induced psychotic disorder, Cocaine induced mood disorder, Cocaine induced anxiety disorder, Cocaine induced sexual dysfunction, Cocaine induced sleep disorder and Cocaine related disorder not otherwise specified; Hallucinogen-related disorders such as Hallucinogen dependence, Hallucinogen abuse, Hallucinogen intoxication, Hallucinogen persisting perception disorder (Flashbacks), Hallucinogen intoxication delirium, Hallucinogen induced psychotic disorder, Hallucinogen induced mood disorder, Hallucinogen induced anxiety disorder and Hallucinogen related disorder not otherwise specified; Inhalant-related disorders such as Inhalant dependence, Inhalant abuse, Inhalant intoxication, Inhalant intoxication delirium, Inhalant induced persisting dementia, Inhalant induced psychotic disorder, Inhalant induced mood disorder, Inhalant induced anxiety disorder and Inhalant related disorder not otherwise specified; Nicotine-related disorders such as Nicotine dependence, Nicotine withdrawal and Nicotine related disorder not otherwise specified; Opiod-related disorders such as Opiod dependence, Opiod abuse, Opiod intoxication, Opiod withdrawal, Opiod intoxication delirium, Opiod induced psychotic disorder, Opiod induced mood disorder, Opiod induced anxiety disorder, Opiod induced sexual dysfunction, Opiod induced sleep disorder and Opiod related disorder not otherwise specified; Phencyclidine (or Phencyclidine like)-related disorder such as Phencyclidine dependence, Phencyclidine abuse, Phencyclidine intoxication, Phencyclidine intoxication delirium, Phencyclidine-induced psychotic disorder, Phencyclidine-induced mood disorder, Phencyclidine-induced anxiety disorder and Phencyclidine related disorder not otherwise specified; Sedative-, Hypnotic-, or Anxiolytic-related disorder such as Sedative, Hypnotic, or Anxiolytic dependence, Sedative, Hypnotic, or Anxiolytic abuse, Sedative, Hypnotic, or Anxiolytic intoxication, Sedative, Hypnotic, or Anxiolytic withdrawal, Sedative, Hypnotic, or Anxiolytic intoxication delirium, Hypnotic, or Anxiolytic withdrawal delirium, Sedative-, Hypnotic-, or Anxiolytic-Persisting Dementia, Sedative-, Hypnotic-, or Anxiolytic-persisting amnestic disorder, Sedative, Hypnotic, or Anxiolytic-induced psychotic disorder, Sedative, Hypnotic, or Anxiolytic-induced mood disorder, Sedative, Hypnotic, or Anxiolytic-induced anxiety disorder, Sedative, Hypnotic, or Anxiolytic-induced sexual dysfunction, Sedative, Hypnotic, or Anxiolytic-induced sleep disorder and Sedative, Hypnotic, or Anxiolytic related disorder not otherwise specified; Polysubstance related disorder such as polysubstance dependence; and other (or unknown) substance related disorders such as anabolic steroids, nitrate inhalants and nitrous oxide.

In still another embodiment compounds of the present invention may be useful in the treatment of sleep disorders which include, but are not limited to, sleep disorders including primary sleep disorders such as Dyssomnias such as Primary Insomnia, Primary Hypersomnia, Narcolepsy, Breathing-related sleep disorders, circadian rhythm sleep disorder and dyssomnia not otherwise specified; primary sleep disorders such as Parasomniaa such as nightmare disorder, sleep tenor disorder, sleepwalking disorder and parasomnia not otherwise specified; Sleep disorder related to another mental disorder such as Insomnia related to another mental disorder and Hypersomnia related to another mental disorder; sleep disorder due to a general medical condition; and substance-induced sleep disorder including the subtypes insomnia type, hypersomnia type, parasomnia type and mixed type.

In a further embodiment compounds of the present invention may be useful in the treatment of eating disorders which include, but are not limited to, eating disorders such as Anorexia Nervosa including subtypes restricting type and binge-eating/purging type; Bulimia Nervosa including the subtypes purging type and nonpurging type; obesity; compulsive eating disorder; binge eating disorder and eating order not otherwise specified.

In still another embodiment compounds of the present invention may be useful in the treatment of Attention deficit hyperactivity disorder which includes, but is not limited to, Attention Deficit/Hyperactivity Disorder including the subtypes Attention Deficit/Hyperactivity Disorder combined type, Attention Deficit/Hyperactivity Disorder Hyperactive-impulse type and Attention Deficit/Hyperactivity Disorder not otherwise specified; Hyperkinetic disorder; disruptive behavior disorders such as conduct disorder including the subtypes childhood-onset type, adolescent-onset type and unspecified onset, oppositional defiant disorder and disruptive behavior disorder not otherwise specified; and Tic disorders such as Tourette's Disorder.

In an embodiment compounds of the present invention may be useful in the treatment of Cognition impairment which includes, but is not limited to, cognition impairment including cognition impairment in other diseases such as schizophrenia, bipolar disorder, depression, other psychiatric disorders and psychotic conditions associated with cognitive impairment, e.g. Alzheimer's disease.

In another embodiment compounds of the present invention may be useful in the treatment of Sexual Dysfunction which includes, but is not limited to, sexual dysfunctions including sexual desire disorders such as hypoactive sexual desire disorder, and sexual aversion disorder; sexual arousal disorders such as Female sexual arousal disorder and male erectile disorder; orgasmic disorders such as female orgasmic disorder, male orgasmic disorder and premature ejaculation; sexual pain disorder such as dyspareunia and vaginismus; sexual function not otherwise specified; paraphilias such as exhibitionism, fetishism, frotteurism, pedophilia, sexual masochism, sexual sadism, transvestic fetishism, voyeurism and paraphilia not otherwise specified; gender identity disorders such as Gender identity disorder in children and gender identity disorder in adolescents or adults; and sexual disorder not otherwise specified.

In still another embodiment compounds of the present invention may be useful in the treatment of obsessive compulsive disorder which includes, but is not limited to, obsessive compulsive disorder including obsessive compulsive disorders, somatoform disorders including body dysmorphic disorder and hyperchondriasis, bulimia nervosa and anorexia nervosa, eating disorders not elsewhere classified such as binge eating, impulse control disorders not elsewhere classified (including intermitted explosive disorder, compulsive buying or shopping, repetitive self-mutilation, onychophagia, psychogenic excoriation, kleptomania, pathological gambling, trichotillomania and internet addiction), paraphilia and nonparaphilic sexual addictions, sydeham's chorea, torticollis, autistic disorders, compulsive hoarding and movement disorders, including Tourett's syndrome.

In yet another embodiment, the compounds or their pharmaceutically acceptable salts according to the present invention are useful in the treatment of the aforementioned diseases, disorders and conditions in combination with at least one other therapeutic agent. The compounds of the present invention may be used in combination with one or more other therapeutic agents in the treatment, prevention, suppression or amelioration of diseases or conditions for which compounds of the present invention or other therapeutic agents may have utility, where the combination of drugs together are safer or more effective than either drug alone.

The other therapeutic agents suitable for combination with the compounds of the present invention include, but are not limited to, other antidepressants, mood stabilizers, antiemetics, testosterone receptor antagonists, testosterone agonists, stimulants, anti-anxiolytic agents, anti-psychotic drugs, anti-obesity drugs, NMDA receptor antagonists, GABA receptor agonists, opioid receptor antagonists, anti-attention deficit hyperactivity disorder agents, anti-addictive disorder agents, anti-alcohol agents, anti-nicotine agents, anti-opiate agents, anti-cocaine agents, opioid mu receptor agonist/opioid kappa receptor antagonist, vasodilatory antihypertensives, anti-Parkinson's-disease agent, anti-schizophernia agent, anti-epilepsy agents, benzodiazepines, non-benzodiazepine hypnotics, barbiturates, other sedative hypnotics, appetite stimulants, zinc, premenstral agents, phosphodiesterase V inhibitors, alpha adrenoreceptor antagonists, prostaglandin agonists, serotonin transport inhibitors, norepinephrine transport inhibitors, dopamine transport inhibitors, dual serotonin/norepinephrine transport inhibitors, triple reuptake inhibitors (inhibiting the reuptake of serotonin, norepinephrine as well as dopamine), 5-$HT_{1A}$ agonists, estrogen agonists, drugs for extrapyramidal side effects and cognitive enhancers.

It is believed that the use of the compounds of the present invention in combination with atleast one or more of the aforementioned other therapeutic agents may provide results greater than that possible from each of these medicaments alone or greater than the combined additive effects produced by these medicaments.

Examples of suitable cognitive enhancers for use in combination with the compounds of the present invention include but are not limited to cholinesterase inhibitors, appetite suppressants, anti-inflammatory agents, anti-diabetic agents, anti-hypertensive agents, anti-lysergic acid diethylamide ("anti-LCD") agent and anti-phencyclidine ("anti-PCP") agent.

EXAMPLES

The invention is explained in detail in the following examples which are given solely for the purpose of illustration only and therefore should not be construed to limit the scope of the invention. Those skilled in the art will readily understand that known variations of the conditions and processes of the following preparative procedures can be used to prepare the compounds of the present invention.

All solvents used in reactions were freshly distilled. Solvents were dried prior to use wherever necessary by standard methods (Perrin, D. D.; Armarego, W. L. F. Purification of Laboratory Chemicals, Pergamon Press: Oxford, 1988). Mass spectra (MS) were obtained by electron spray ionization (ESI) eV using Applied biosystem 4000 Q TRAP. $^1$H NMR were recorded on Bruker 400 MHz Avance II NMR spectrometer in $CDCl_3$ (until and unless specified). Chemical shifts are reported as δ values in parts per million (ppm), relative to TMS as internal standard. All coupling constant (J) values are given in Hz.

ABBREVIATIONS

The following abbreviations are employed in the examples and elsewhere herein:

| | |
|---|---|
| $^1$H NMR | proton nuclear magnetic resonance |
| bs | broad singlet |
| C | centigrade |
| $CDCl_3$ | deuterated chloroform |
| $CD_3OD$ | deuterated methanol |
| cm | centimeter |
| CMC | carboxymethyl cellulose |
| DCM | dichloromethane |
| DCE | dichloroethane |
| d | doublet |
| dd | doublet of doublet |
| DMF | dimethylformamide |
| DMSO | dimethylsulfoxide |
| ESIMS | electron spray ionization mass Spectroscopy |
| EtOAc | ethylacetate |
| $Et_3N$ | triethylamine |
| g | gram(s) |
| (g) | gaseous |
| h | hour(s) |
| HCl | hydrochloric acid |
| Hz | hertz |
| J | coupling constant |
| $K_2CO_3$ | potassium carbonate |
| LDA | lithium diisopropylamide |
| LiHMDS | lithium Hexamethyldisilazide |
| m | multiplet |
| M | molar |
| MeOH | methanol |
| mg | milligram |
| MHz | mega hertz |
| min | minutes |
| mL | milliliter |
| mmol | millimoles |
| $Na_2SO_4$ | sodium sulphate |
| NMR | nuclear magnetic resonance |
| PCC | pyridinium chlorochromate |
| PDC | pyridinium dichromate |
| Pet. ether | petroleum ether |
| r. t. | room temperature |
| s | singlet |
| t | triplet |
| $^tBu$ | tert-butyl |
| TEMPO | (2,2,6,6-Tetramethyl-piperidin-1-yl)oxyl, free radical |
| THF | tetrahydrofuran |
| TLC | thin layer chromatography |
| TMS | tetramethylsilane |

Preparation 1: Preparation of tert-butyl 6-(3,4-dichlorobenzoyl)-3-azabicyclo[3.1.0]hexane-3-carboxylate Step-1: Preparation of tert-butyl 6-((3,4-dichlorophenyl)(hydroxy)methyl)-3-azabicyclo[3.1.0]hexane-3-carboxylate To a solution of tert-butyl 6-formyl-3-azabicyclo[3.1.0]hexane-3-carboxylate (6.00 g, 28.17 mmol, prepared according to procedure described in Synlett, 1996, 1097-1099) in dry THF (50 mL) at −78° C. under nitrogen atmosphere, was added 3,4-dichlorophenylmagnesium bromide (56.34 mL, 56.34 mmol, 1M in THF). The reaction mixture was allowed to come to r.t. Saturated solution of ammonium chloride (20 mL) was added slowly to the reaction mixture. The crude compound was extracted with ethylacetate (100 mL). The organic layer was washed with water, separated, dried over $Na_2SO_4$ and concentrated in vacuo to afford the crude compound which was purified by column chromatography (silica gel, 3:7 EtOAc:Pet Ether) to afford tert-butyl 6-(3,4-dichlorophenyl)hydroxymethyl)-3-azabicyclo[3.1.0]hexane-3-carboxylate (8.12 g, 80%) as a white solid.

ESIMS (m/z): 357 (M−1)

Step-2: Preparation of tert-butyl 6-(3,4-dichlorobenzoyl)-3-azabicyclo[3.1.0]hexane-3-carboxylate Oxalyl chloride (2.35 mL, 27.30 mmol) was added to a solution of DMSO (4.20 mL, 59.04 mmol) in dry DCM (20 mL) at −78° C. under nitrogen atmosphere. The reaction mixture was stirred for 30 min. at the same temperature and then a solution of 6-((3,4-dichlorophenyl)(hydroxy)methyl)-3-azabicyclo[3.1.0]hexane-3-carboxylate (8.0 g, 22.4 mmol) obtained in step-1 of preparation 1, in dry DCM (15 mL) was added. The reaction mixture was stirred at the same temperature for 1 h. Et$_3$N (15.81 mL, 113.74 mmol) was added and the reaction mixture was allowed to come to r.t. The crude compound was extracted with DCM (100 mL). The organic layer was separated, washed with 10% HCl (20 mL), sodium bicarbonate solution (20 mL), water (15 mL), dried over Na$_2$SO$_4$ and concentrated in vacuo to afford crude product which was purified by column chromatography (silica gel, 1:9 EtOAc:Pet Ether) to afford tert-butyl 6-(3,4-dichlorobenzoyl)-3-azabicyclo[3.1.0]hexane-3-carboxylate (7.0 g, 86%) as a white solid.

ESIMS (m/z): 357.5 (M+1)

Example 1

Preparation of hydrochloric acid salt of 3-azabicyclo[3.1.0]hexan-6-yl(3,4-dichlorophenyl)methanone O-ethyl oxime

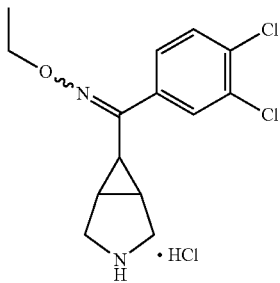 [SMILES: CCON=C(c1ccc(Cl)c(Cl)c1)C1C2CNCC21 ; "· HCl"]

Step 1: Preparation of tert-butyl 6-((3,4-dichlorophenyl)(hydroxyimino)methyl)-3-azabicyclo[3.1.0]hexane-3-carboxylate To a solution of tert-butyl 6-(3,4-dichlorobenzoyl)-3-azabicyclo[3.1.0]hexane-3-carboxylate (800 mg, 2.25 mmol) obtained in step-2 of preparation 1, in ethanol (15 mL) under nitrogen atmosphere, were added hydroxylamine hydrochloride (313 mg, 4.50 mmol) and pyridine (0.91 mL, 11.30 mmol). The reaction mixture was refluxed for 5 h. After completion of the reaction as confirmed by TLC, the solvent was evaporated. The crude compound was extracted with ethyl acetate (70 mL). The organic layer was separated, washed with 5% HCl (5 mL), water (10 mL), dried over Na$_2$SO$_4$ and concentrated in vacuo to afford crude product which was purified by column chromatography (silica gel, 2:3 EtOAc:Pet Ether) to afford pure tert-butyl 6-((3,4-dichlorophenyl)(hydroxyimino)methyl)-3-azabicyclo[3.1.0]hexane-3-carboxylate (740 mg, 92%) as a viscous oil as a mixture of isomers.

ESIMS (m/z): 370.7 (M−1)

Step 2: Preparation of tert-butyl 6-((3,4-dichlorophenyl)(ethoxyimino)methyl)-3-azabicyclo[3.1.0]hexane-3-carboxylate To a suspension of sodium hydride (35 mg, 0.87 mmol, 60% suspension in mineral oil) in dry DMF (3 mL) at 0° C. under nitrogen atmosphere, was added a solution of tert-butyl 6-((3,4-dichlorophenyl)(hydroxyimino)methyl)-3-azabicyclo[3.1.0]hexane-3-carboxylate (200 mg, 0.54 mmol), obtained in step-1 of example 1, in DMF (3 mL) The reaction mixture was stirred at the same temperature for 30 min followed by the addition of ethyl iodide (0.09 mL, 1.1 mmol). The reaction mixture was stirred at room temperature overnight. After completion of the reaction as confirmed by TLC, the reaction mixture was quenched by saturated solution of ammonium chloride and the crude compound was extracted with ethyl acetate. The organic layer was washed with water, separated, dried over anhydrous sodium sulphate and concentrated in vacuo to afford tert-butyl 6-((3,4-dichlorophenyl)(ethoxyimino)methyl)-3-azabicyclo[3.1.0]hexane-3-carboxylate (150 mg, 70%) as a viscous oil which was used without any purification for the next step.

ESIMS (m/z): 400.2 (M+1), 399.8 (M+)

Step 3: Preparation of hydrochloric acid salt of 3-azabicyclo[3.1.0]hexan-6-yl(3,4-dichlorophenyl)methanone O-ethyl oxime HCl (g) was bubbled through a solution of tert-butyl 6-((3,4-dichlorophenyl)(ethoxyimino)methyl)-3-azabicyclo[3.1.0]hexane-3-carboxylate (100 mg, 0.25 mmol) obtained in step-2 of example 1 in dry DCM (5 mL). After the completion of the reaction as confirmed by TLC, the reaction mixture was purged with excess of nitrogen. The solvent was removed in vacuo to afford a gummy solid which was titurated with hexane to afford hydrochloric acid salt of 3-azabicyclo[3.1.0]hexan-6-yl(3,4-dichlorophenyl)methanone O-ethyl oxime (75 mg, 86%) as a white solid as a mixture of isomers.

$^1$H NMR (400 MHz, CD$_3$OD): δ 1.19 and 1.31 (two triplets, J$_1$=7.2 Hz, J$_2$=7.2 Hz, 3H), 1.81 and 2.02 (two triplets, J$_1$=4.0 Hz, J$_2$=4.0 Hz, 1H), 2.15-2.17 and 2.33-2.34 (two multiplets, 2H), 3.51-3.62 (m, 4H), 4.06 and 4.22 (two quatrets, J$_1$=6.8 Hz, J$_2$=7.2 Hz, 2H), 7.44-7.48 (m, 1H), 7.55 and 7.57 (two doublets, J$_1$=10.0 Hz, J$_2$=10.0 Hz, 1H), 7.69 and 7.71 (two doublets, J$_1$=2.0 Hz, J$_2$=2.0 Hz, 1H).

ESIMS (m/z): 300.5 (M+1)

Example 2

Preparation of hydrochloric acid salt of 3-azabicyclo[3.1.0]hexan-6-yl(3,4-dichlorophenyl)methanone O-phenyl oxime

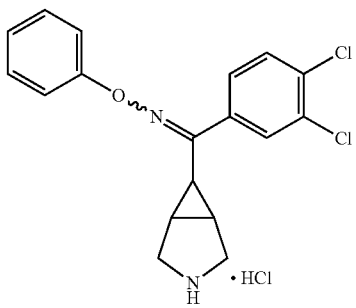 [SMILES: Clc1ccc(C(=NOc2ccccc2)C2C3CNCC32)cc1Cl ; "· HCl"]

Step 1: Preparation of tert-butyl 6-((3,4-dichlorophenyl)(phenoxyimino)methyl)-3-azabicyclo[3.1.0]hexane-3-carboxylate To a solution of tert-butyl 6-(3,4-dichlorobenzoyl)-3-azabicyclo[3.1.0]hexane-3-carboxylate (200 mg, 0.56 mmol)

obtained in step-2 of preparation 1, in ethanol (10 mL) under nitrogen atmosphere, were added O-phenylhydroxylamine hydrochloride (164 mg, 1.12 mmol) and pyridine (0.23 mL, 2.86 mmol). The reaction mixture was refluxed for 5 h. After completion of the reaction as confirmed by TLC, the solvent was evaporated. The crude compound was extracted with ethyl acetate (20 mL). The organic layer was separated, washed with 5% HCl (5 mL), water (10 mL), dried over $Na_2SO_4$ and concentrated in vacuo to afford crude product which was purified by column chromatography (silica gel, 3:7 EtOAc:Pet Ether) to afford pure tert-butyl 6-((3,4-dichlorophenyl)(phenoxyimino)methyl)-3-azabicyclo[3.1.0]hexane-3-carboxylate (180 mg, 71%) as a gummy solid as a mixture of isomers.

ESIMS (m/z): 449.9 (M+2), 447.8 (M+).

Step 2: Preparation of hydrochloric acid salt of 3-azabicyclo[3.1.0]hexan-6-yl(3,4-dichlorophenyl)methanone O-phenyl oxime HCl (g) was bubbled through a solution of tert-butyl 6-((3,4-dichlorophenyl)(phenoxyimino)methyl)-3-azabicyclo[3.1.0]hexane-3-carboxylate (160 mg, 0.36 mmol) obtained in step-1 of example 2 in dry DCM (5 mL). After the completion of the reaction as confirmed by TLC, the reaction mixture was purged with excess of nitrogen. The solvent was removed in vacuo to afford hydrochloric acid salt of 3-azabicyclo[3.1.0]hexan-6-yl(3,4-dichlorophenyl)methanone O-phenyl oxime as a gummy solid which was titurated with hexane to afford (125 mg, 91%) as a white solid as a mixture of isomers.

$^1$H NMR (400 MHz, $CD_3OD$): δ 1.95 and 2.52 (two triplets, $J_1$=4.0 Hz, $J_2$=4.0 Hz, 1H), 2.28-2.30 (m, 2H), 3.54-3.71 (m, 4H), 7.00-7.10 (m, 2H), 7.20-7.35 (m, 3H), 7.55-7.67 (m, 2H), 7.77 and 7.81 (two doublets, $J_1$=1.96 Hz, $J_2$=1.96 Hz, 1H)

ESIMS (m/z): 348 (M+1)

Example 3

Preparation of hydrochloric acid salt of 3-azabicyclo[3.1.0]hexan-6-yl(3,4-dichlorophenyl)methanone O-methyl oxime

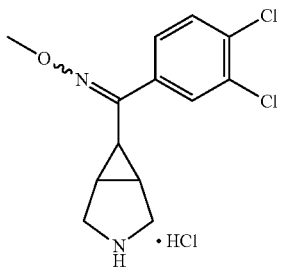 [SMILES: CON=C(c1ccc(Cl)c(Cl)c1)C1C2CNCC21 ; "· HCl"]

Step 1: Preparation of tert-butyl 6-((3,4-dichlorophenyl)(methoxyimino)methyl)-3-azabicyclo[3.1.0]hexane-3-carboxylate To a solution of tert-butyl 6-(3,4-dichlorobenzoyl)-3-azabicyclo[3.1.0]hexane-3-carboxylate (100 mg, 0.28 mmol) obtained in step-2 of preparation 1, in ethanol (5 mL) under nitrogen atmosphere, were added pyridine (0.11 mL, 1.37 mmol) and O-methylhydroxylamine hydrochloride (47 mg, 0.56 mmol). The reaction mixture was refluxed for 5 h. After completion of the reaction as confirmed by TLC, the solvent was evaporated. The crude compound was extracted with ethyl acetate (20 mL). The organic layer was separated, washed with 5% HCl (5 mL), water (10 mL), dried over $Na_2SO_4$ and concentrated in vacuo to afford crude product which was purified by column chromatography (silica gel, 2:3 EtOAc:Pet Ether) to afford pure tert-butyl 6-((3,4-dichlorophenyl)(methoxyimino)methyl)-3-azabicyclo[3.1.0]hexane-3-carboxylate (100 mg, 92%) as a viscous oil as mixture of isomers.

ESIMS (m/z): 387.5 (M+2), 385.5 (M+)

Step 2: Preparation of hydrochloric acid salt of 3-azabicyclo[3.1.0]hexan-6-yl(3,4-dichlorophenyl)methanone O-methyl oxime HCl (g) was bubbled through a solution of tert-butyl 6-((3,4-dichlorophenyl)(methoxyimino)methyl)-3-azabicyclo[3.1.0]hexane-3-carboxylate (90 mg, 0.23 mmol) obtained in step-1 of example 3 in dry DCM (5 mL). After the completion of the reaction as confirmed by TLC, the reaction mixture was purged with excess of nitrogen. The solvent was removed in vacuo to afford a gummy solid which was titurated with hexane to afford hydrochloric acid salt of 3-azabicyclo[3.1.0]hexan-6-yl(3,4-dichlorophenyl)methanone O-methyl oxime (65 mg, 86%) as a white solid as a mixture of isomers.

$^1$H NMR (400 MHz, $CD_3OD$): δ 1.81 and 2.03 (two triplets, $J_1$=3.6 Hz, $J_2$=4.4 Hz, 1H), 2.13-2.15 and 2.33-2.35 (two multiplets, 2H), 3.50-3.61 (m, 4H), 3.80 and 3.97 (two singlets, 3H), 7.41-7.47 (m, 1H), 7.54-7.59 (merged doublets, 1H), 7.68-7.69 (merged doublets, 1H).

ESIMS (m/z): 285.2 (M+)

Example 4

Preparation of 3-azabicyclo[3.1.0]hexan-6-yl(3,4-dichlorophenyl)methanone O-methyl oxime

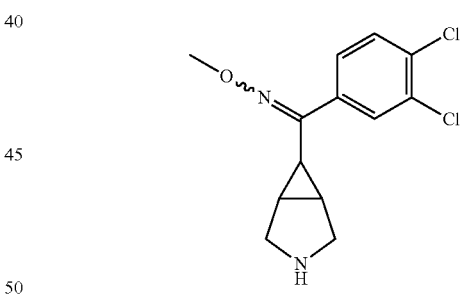

To a solution of hydrochloric acid salt of 3-azabicyclo[3.1.0]hexan-6-yl(3,4-dichlorophenyl)methanone O-methyl oxime (64 mg, 0.19 mmol) obtained in step-2 of example 3 in ethyl acetate (15 mL), was added saturated sodium bicarbonate solution (10 mL). The reaction mixture was stirred at r.t. for 30 min. The organic layer was separated, dried over $Na_2SO_4$ and concentrated in vacuo to afford pure 3-azabicyclo[3.1.0]hexan-6-yl(3,4-dichlorophenyl)methanone O-methyl oxime (53 mg, 96%) as an oil as a mixture of isomers.

$^1$H NMR (400 MHz, $CDCl_3$): δ 1.46 and 1.83 (two triplets, $J_1$=3.2 Hz, $J_2$=4.0 Hz, 1H), 1.67-1.70 and 1.90-2.00 (two multiplets, 2H), 2.92-2.98 and 3.08-3.16 (two multiplets, 4H), 3.80 and 3.96 (two singlets, 3H), 7.26-7.30 (m, 1H), 7.41-7.46 (m, 1H), 7.52 and 7.55 (two doublets, $J_1$=2.0 Hz, $J_2$=2.0 Hz, 1H)

ESIMS (m/z): 286.6 (M+1), 285.2 (M+)

Example 5

Preparation of hydrochloric acid salt of 1-(4-chlorophenyl)-3-azabicyclo[3.1.0]hexane-6-carbaldehyde O-methyl oxime

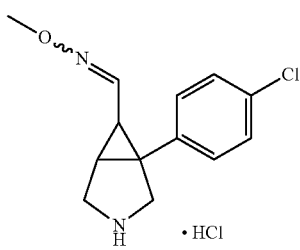 [SMILES: CON=CC1C2CNCC12c1ccc(Cl)cc1 ; "· HCl"]

Step 1: Preparation of tert-butyl 1-(4-chlorophenyl)-6-((methoxyimino)methyl)-3-azabicyclo[3.1.0]hexane-3-carboxylate To a solution of tert-butyl 1-(4-chlorophenyl)-6-formyl-3-azabicyclo[3.1.0]hexane-3-carboxylate (609 mg, 1.99 mmol, prepared from maleimide and 4-chloroaniline according to the methods described in WO 2009141412 and WO 2008074716), in ethanol (10 mL) under nitrogen atmosphere, were added pyridine (0.8 mL, 9.9 mmol) and O-methylhydroxylamine hydrochloride (332.4 mg, 3.98 mmol). The reaction mixture was refluxed for 5 h. After completion of the reaction as confirmed by TLC, the solvent was evaporated. The crude compound was extracted with ethyl acetate (20 mL). The organic layer was separated, washed with 5% HCl (5 mL), water (10 mL), dried over $Na_2SO_4$ and concentrated in vacuo to afford crude product which was purified by column chromatography (silica gel, 2:3 EtOAc:Pet Ether) to afford pure tert-butyl 1-(4-chlorophenyl)-6-((methoxyimino)methyl)-3-azabicyclo[3.1.0]hexane-3-carboxylate (430 mg, 63%) as a viscous oil as mixture of isomers.

ESIMS (m/z): 351.8 (M+1)

Step 2: Preparation of hydrochloric acid salt of 1-(4-chlorophenyl)-3-azabicyclo[3.1.0]hexane-6-carbaldehyde O-methyl oxime HCl (g) was bubbled through a solution of tert-butyl 1-(4-chlorophenyl)-6-((methoxyimino)methyl)-3-azabicyclo[3.1.0]hexane-3-carboxylate (210 mg, 0.598 mmol) obtained in step-1 of example 5 in dry DCM (10 mL). After the completion of the reaction as confirmed by TLC, the reaction mixture was purged with excess of nitrogen. The solvent was removed in vacuo to afford a gummy solid which was titurated with hexane to afford hydrochloric acid salt of 1-(4-chlorophenyl)-3-azabicyclo[3.1.0]hexane-6-carbaldehyde O-methyl oxime (140 mg, 81%) as white solid as mixture of isomers.

$^1$H NMR (400 MHz, $CD_3OD$): δ 2.15-2.18 and 2.75-2.78 (two multiplets, 1H), 2.63 and 2.67 (two triplets, $J_1$=4.0 Hz, $J_2$=4.0 Hz, 1H), 3.43-3.47 (m, 1H), 3.62-3.66 (m, 1H), 3.69 and 3.85 (two singlets, 3H), 3.75-3.80 (m, 1H), 3.88-3.96 (m, 1H), 5.93 and 6.70 (two doublets, $J_1$=7.6 Hz, $J_2$=7.6 Hz, 1H), 7.34-7.41 (m, 4H).

ESIMS (m/z): 252.4 (M+2)

Example 6

Preparation of hydrochloric acid salt of 1-(3,4-dichlorophenyl)-3-azabicyclo[3.1.0]hexane-6-carbaldehyde O-ethyl oxime

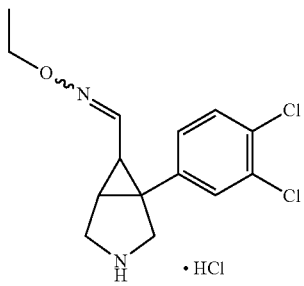 [SMILES: CCON=CC1C2CNCC12c1ccc(Cl)c(Cl)c1 ; "· HCl"]

Step 1: Preparation of tert-butyl 1-(3,4-dichlorophenyl)-6-((hydroxyimino)methyl)-3-azabicyclo[3.1.0]hexane-3-carboxylate To a solution of tert-butyl 1-(3,4-dichlorophenyl)-6-formyl-3-azabicyclo[3.1.0]hexane-3-carboxylate (200 mg, 0.56 mmol, prepared from maleimide and 3,4-dichloroaniline according to the methods described in WO 2009141412 and WO 2008074716), in ethanol (10 mL) under nitrogen atmosphere were added hydroxylamine hydrochloride (78 mg, 1.12 mmol) and pyridine (0.23 mL, 2.86 mmol). The reaction mixture was refluxed for 5 h. After completion of the reaction as confirmed by TLC, the solvent was evaporated. The crude compound was extracted with ethyl acetate (70 mL). The organic layer was separated, washed with 5% HCl (5 mL), water (10 mL), dried over $Na_2SO_4$ and concentrated in vacuo to afford crude product which was purified by column chromatography (silica gel, 1:4 EtOAc:Pet Ether) to afford pure tert-butyl 1-(3,4-dichlorophenyl)-6-((hydroxyimino)methyl)-3-azabicyclo[3.1.0]hexane-3-carboxylate (152 mg, 73%) as a viscous oil as a mixture of isomers.

ESIMS (m/z): 315.4 (M-$^t$Bu)

Step 2: Preparation of tert-butyl 1-(3,4-dichlorophenyl)-6-((ethoxyimino)methyl)-3-azabicyclo[3.1.0]hexane-3-carboxylate To a suspension of sodium hydride (23 mg, 0.96 mmol, 60% suspension in mineral oil) in dry DMF (2 mL) at 0° C. under nitrogen atmosphere, was added a solution of tert-butyl 1-(3,4-dichlorophenyl)-6-((hydroxyimino)methyl)-3-azabicyclo[3.1.0]hexane-3-carboxylate (140 mg, 0.38 mmol), obtained in step-1 of example 6, in DMF (2 mL). The reaction mixture was stirred at the same temperature for 30 min followed by the addition of ethyl iodide (0.06 mL, 0.74 mmol). The reaction mixture was stirred at room temperature for 3 h. After completion of the reaction as confirmed by TLC, the reaction mixture was quenched by saturated solution of ammonium chloride and the crude compound was extracted with ethyl acetate. The organic layer was washed with water, separated, dried over anhydrous sodium sulphate and concentrated in vacuo to afford crude product which was purified by column chromatography (silica gel, 1:9 EtOAc: Pet Ether) to afford pure tert-butyl 1-(3,4-dichlorophenyl)-6-((ethoxyimino)methyl)-3-azabicyclo[3.1.0]hexane-3-carboxylate (75 mg, 50%) as a viscous oil as a mixture of isomers.

ESIMS (m/z): 400.7 (M+1), 399.8 (M+)

Step 3: Preparation of hydrochloric acid salt of 1-(3,4-dichlorophenyl)-3-azabicyclo[3.1.0]hexane-6-carbaldehyde O-ethyl oxime HCl (g) was bubbled through a solution of tert-butyl 1-(3,4-dichlorophenyl)-6-((ethoxyimino)methyl)-3-azabicyclo[3.1.0]hexane-3-carboxylate (70 mg, 0.17 mmol) obtained in step-2 of example 6 in dry DCM (5 mL). After the completion of the reaction as confirmed by TLC, the reaction mixture was purged with excess of nitrogen. The solvent was removed in vacuo to afford a gummy solid which was titurated with hexane to afford hydrochloric acid salt of 1-(3,4-dichlorophenyl)-3-azabicyclo[3.1.0]hexane-6-carbaldehyde O-ethyl oxime (39 mg, 95%) as a white solid as a mixture of isomers.

$^1$H NMR (400 MHz, CD$_3$OD): δ 1.09 and 1.25 (two triplets, $J_1$=7.2 Hz, $J_2$=7.2 Hz, 3H), 2.16-2.19 and 2.75-2.78 (two multiplets, 1H), 2.66 and 2.73 (two triplets, $J_1$=4.0 Hz, $J_2$=4.0 Hz, 1H), 3.45-3.49 (m, 1H), 3.46 and 3.48 (two doublets, $J_1$=11.6 Hz, $J_2$=11.6 Hz, 1H), 3.63 (d, J=11.6 Hz, 1H), 3.76 and 3.79 (two doublets, $J_1$=4.0 Hz, $J_2$=4.4 Hz, 1H), 3.90 and 3.96 (two doublets, $J_1$=6.8 Hz, $J_2$=3.60 Hz, 1H), 3.92 and 4.11 (two quatrets, $J_1$=7.2 Hz, $J_2$=7.2 Hz, 2H), 5.98 and 6.80 (two doublets, $J_1$=7.2 Hz, $J_2$=7.2 Hz, 1H), 7.27-7.32 (m, 1H), 7.53 and 7.54 (two doublets, $J_1$=8.4 Hz, $J_2$=8.4 Hz, 1H), 7.57 and 7.59 (two doublets, $J_1$=2.0 Hz, $J_2$=2.0 Hz, 1H)

ESIMS (m/z): 300.6 (M+1), 299.3 (M+)

Example 7

Preparation of hydrochloric acid salt of 1-(3,4-dichlorophenyl)-3-azabicyclo[3.1.0]hexane-6-carbaldehyde O-methyl oxime

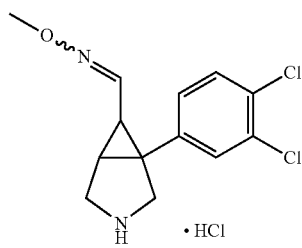 [SMILES: CON=CC1C2CNCC12c1ccc(Cl)c(Cl)c1 ; "· HCl"]
· HCl

Step 1: Preparation of tert-butyl 1-(3,4-dichlorophenyl)-6-((methoxyimino)methyl)-3-azabicyclo[3.1.0]hexane-3-carboxylate To a solution of tert-butyl 1-(3,4-dichlorophenyl)-6-formyl-3-azabicyclo[3.1.0]hexane-3-carboxylate (2.50 g, 7.02 mmol, prepared from maleimide and 3,4-dichloroaniline according to the methods described in WO 2009141412 and WO 2008074716), in ethanol (40 mL) under nitrogen atmosphere, were added pyridine (2.82 mL, 35.04 mmol) and O-methylhydroxylamine hydrochloride (1.17 g, 14.01 mmol). The reaction mixture was refluxed for 5 h. After completion of the reaction as confirmed by TLC, the solvent was evaporated. The crude compound was extracted with ethyl acetate (20 mL). The organic layer was separated, washed with 5% HCl (5 mL), water (10 mL), dried over Na$_2$SO$_4$ and concentrated in vacuo to afford crude product which was purified by column chromatography (silica gel, 1:9 EtOAc:Pet Ether) to afford pure tert-butyl 1-(3,4-dichlorophenyl)-6-((methoxyimino)methyl)-3-azabicyclo[3.1.0]hexane-3-carboxylate (2.45 g, 90%) as a viscous oil as a mixture of isomers.

ESIMS (m/z): 387.7 (M+2), 385.7 (M+)

Step 2: Preparation of hydrochloric acid salt of 1-(3,4-dichlorophenyl)-3-azabicyclo[3.1.0]hexane-6-carbaldehyde O-methyl oxime HCl (g) was bubbled through a solution of tert-butyl 1-(3,4-dichlorophenyl)-6-((methoxyimino)methyl)-3-azabicyclo[3.1.0]hexane-3-carboxylate (2.40 g, 6.23 mmol) obtained in step-1 of example 7 in dry DCM (40 mL). After the completion of the reaction as confirmed by TLC, the reaction mixture was purged with excess of nitrogen. The solvent was removed in vacuo to afford a gummy solid which was titurated with hexane to afford hydrochloric acid salt of 1-(3,4-dichlorophenyl)-3-azabicyclo[3.1.0]hexane-6-carbaldehyde O-methyl oxime (1.95 g, 97%) as a white solid as a mixture of isomers.

$^1$H NMR (400 MHz, CD$_3$OD): δ 2.17-2.20 and 2.75-2.78 (two multiplets, 1H), 2.66 and 2.72 (two triplets, $J_1$=8.0 Hz, $J_2$=4.0 Hz, 1H), 3.45-3.49 and 3.89-3.95 (two multiplets, 2H), 3.63 and 3.78 (two dd, $J_1$=12.0 and 14.8 Hz, $J_2$=3.2 and 12.0 Hz, 2H), 3.69 and 3.86 (two singlets, 3H), 5.97 and 6.76 (two doublets, $J_1$=7.6 Hz, $J_2$=7.2 Hz, 1H), 7.27-7.31 (m, 1H), 7.52 and 7.54 (two doublets, $J_1$=5.2 Hz, $J_2$=5.6 Hz, 1H), 7.58 and 7.59 (two doublets, $J_1$=2.0 Hz, $J_2$=2.0 Hz, 1H)

ESIMS (m/z): 286.6 (M+1), 285.3 (M+)

The compounds listed in Table II were prepared essentially following the procedures described for Examples 1 to 7:

TABLE II

| Example No. | -R$^1$ | -R$^2$ | -R$^3$ | -R$^4$ | ESIMS (m/z) |
|---|---|---|---|---|---|
| 1 | H | 3,4-dichlorophenyl | H | H | 272.4 (M + 1), 271.5 (M+) |

TABLE II-continued

| Example No. | -R¹ | -R² | -R³ | -R⁴ | ESIMS (m/z) |
|---|---|---|---|---|---|
| 2 | H | phenyl | H | $CH_3$ | 217.5 (M + 1), 216.4 (M+) |
| 3 | H | 2-naphthyl | H | $CH_3$ | 268.4 (M + 2), 267.1 (M + 1) |
| 4 | H | 3,4-dichlorophenyl | H | $CH_2-CH=CH_2$ | 311.9 (M + 1) |
| 5 | H | 3,4-dichlorophenyl | H | cyclopropylmethyl | 326.4 (M + 1), 325.2 (M+) |
| 6 | H | 3,4-dichlorophenyl | H | benzyl | 362.5 (M + 1), 361.4 (M+) |
| 7 | H | 3,4-dichlorophenyl | H | 4-fluorobenzyl | 381.3 (M + 2), 379.2 (M+) |
| 8 | H | 3,4-dichlorophenyl | H | 4-(trifluoromethyl)benzyl | 430.7 (M + 1), 429.4 (M+) |

TABLE II-continued

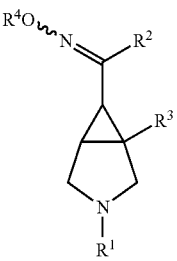

| Example No. | -R¹ | -R² | -R³ | -R⁴ | ESIMS (m/z) |
|---|---|---|---|---|---|
| 9 | H | H | 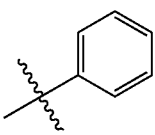 [SMILES: *c1ccccc1] | CH₃ | 217.3 (M + 1) |
| 10 | H | H | 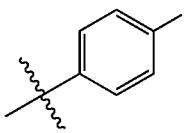 | CH₃ | 236.6 (M + 2), 235.4 (M + 1) |
| 11 | H | H | 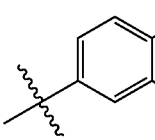 | 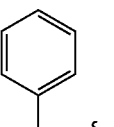 | 363.5 (M + 2), 361.8 (M + 1) |
| 12 | H | H | 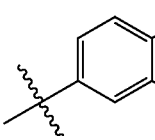 | 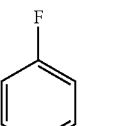 | 380.5 (M + 1), 379.8 (M+) |

The biological activities of the compounds of the present invention were demonstrated by following test procedures.

In Vivo Studies

Forced Swim Test:

This test was conducted according to the method of Li, X., et al., Metabotropic Glutamate 5 Receptor Antagonism Is Associated with Antidepressant-Like Effects in Mice. J Pharmacol Exp Ther., 319(1):254-259 (2006), with slight modifications.

A test compound was suspended in 0.25% CMC, unless otherwise specified, and this solution was orally administered to male SWISS albino mice (7 to 9 week old). 15 min later, the mice were placed in a water tank having a water depth of 15 cm and a water temperature of 25±1° C. and immediately thereafter allowed to swim for 6 min. Then, a time during which the mouse was immobile (immobility time) was measured for the last 4 min.

In this experiment, the animals treated with the test compounds exhibited a reduction in immobility time. This demonstrates that the test compounds are useful as antidepressants.

Cleversys Software (Forced Swim Scan) was used for carrying out Forced Swim Test in mice.

TABLE III

Forced Swim Test results

| Compound | % decrease in immobility time (dose 32 mg/kg) |
|---|---|
| [structure: methoxyimino-(3,4-dichlorophenyl)methyl-3-azabicyclo[3.1.0]hexane·HCl] | 80.0 ± 3.8[z] |
| [structure: 1-(3,4-dichlorophenyl)-methoxyiminomethyl-3-azabicyclo[3.1.0]hexane·HCl] | 87.5 ± 4.1[z] |
| [structure: 1-(3,4-dichlorophenyl)-ethoxyiminomethyl-3-azabicyclo[3.1.0]hexane·HCl] | 83.1 ± 9.6 |
| [structure: 1-(4-chlorophenyl)-methoxyiminomethyl-3-azabicyclo[3.1.0]hexane·HCl] | 50.2 ± 14.7[z] |
| [structure: 1-(4-fluorophenyl)-methoxyiminomethyl-3-azabicyclo[3.1.0]hexane·HCl] | 55.1 ± 13.0[z] |
| [structure: 1-phenyl-methoxyiminomethyl-3-azabicyclo[3.1.0]hexane·HCl] | 60.4 ± 12.6 |

[z]Vehicle—De-ionized water

In Vitro Studies

Binding Assay
1. Norepinephrine Binding Assay

The Membrane protein of 0.4 mL size vial, with protein concentration of 3.0 mg/ml was bought from Perkin Elmer, stored in −80° C. until required.

[$^3$H]-Nisoxetine Binding Assay:

Each well of 96 well microtitre plate was set up to contain the following:

| | |
|---|---|
| 25 μl | Test compound (1-1000 nM), assay buffer (total binding) or 10 μM Desipramine (Non specific binding) |
| 25 μl | 4 nM [N-methyl-$^3$H]-Nisoxetine hydrochloride (60-90 Ci/mmol, from Perkin Elmer) |
| 200 μl | Membrane (3 μg/200 μl) diluted in assay buffer (50 mM Tris-HCl pH 7.4 containing 120 mM NaCl and 5 mM KCl) |

The microtitre plates were incubated at 4° C. for 60 mins; reaction was stopped by filtration in GF/B filter plate (pre-soaked in 0.5% Polyethylenimine) and then added 50 μl of microscint 40. Radioactivity was measured on Liquid Scintillation counter (Perkin Elmer).

2. Serotonin Binding Assay

The Membrane protein of 0.4 mL size vial, with protein concentration of 9.0 mg/ml was bought from Perkin Elmer, stored in −80° C. until required.

[$^3$H]-Citalopram Binding Assay:

Each well of 96 well microtitre plate was set up to contain the following:

| | |
|---|---|
| 25 μl | Test compound (1-1000 nM), assay buffer (total binding) or 100 nM Paroxetine (Non specific binding) |
| 25 μl | 2 nM [$^3$H]-Citalopram (70-90 Ci/mmol, from Perkin Elmer, Inc.) |
| 200 μl | Membrane (9 μg/200 μl) diluted in assay buffer (50 mM Tris-HCl pH 7.4 containing 120 mM NaCl and 5 mM KCl) |

The microtitre plates were incubated at 25° C. for 60 min; reaction was stopped by filtration in GF/B filter plate (pre-soaked in 0.5% Polyethylenimine) and then added 50 μL of microscint 40. Radioactivity was measured on Liquid Scintillation counter (Perkin Elmer).

3. Dopamine Binding Assay

The Membrane protein of 0.4 mL size vial, with protein concentration of 12 mg/mL was bought from Perkin Elmer, stored in −80° C. until required.

[³H]-WIN35,428 Binding Assay:

Each well of 96 well microtitre plate was set up to contain the following:

| | |
|---|---|
| 25 µl | Test compound (1-1000 nM), assay buffer (total binding) or 100 µM Nomifensine (Non specific binding) |
| 25 µl | 10 nM [³H] - WIN35, 428 (60-90 Ci/mmol, from Perkin Elmer) |
| 200 µl | Membrane (12 µg/200 µl) diluted in assay buffer (50 mM Tris-HCl pH 7.4 containing 100 mM NaCl) |

The microtitre plates were incubated at 4° C. for 120 min; reaction was stopped by filtration in GF/B filter plate (pre-soaked in 0.5% Polyethylenimine) and then added 50 µL of microscint 40. Radioactivity was measured on Liquid Scintillation counter (Perkin Elmer).

TABLE IV

In-vitro Data

| Compound | SERT % Citalopram displacement | | NET % Nisoxetine displacement | | DAT % WIN 35428 displacement | |
|---|---|---|---|---|---|---|
| | 100 nM | 1 µM | 100 nM | 1 µM | 100 nM | 1 µM |
| 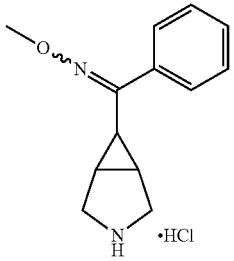 [SMILES: CON=C(c1ccccc1)C1C2CNCC21 ; Cl] | 18.36 | 27.48 | NE | NE | NE | NE |
| 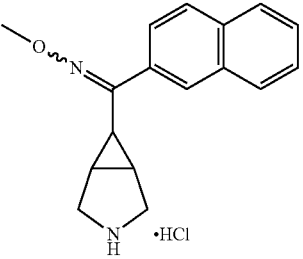 [SMILES: CON=C(c1ccc2ccccc2c1)C1C2CNCC21 ; Cl] | 77.23 | 93.40 | 21.76 | 60.49 | NE | NE |
| 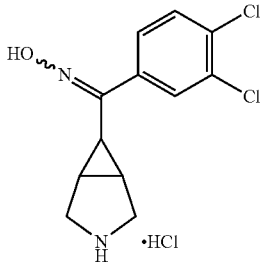 [SMILES: ON=C(c1ccc(Cl)c(Cl)c1)C1C2CNCC21 ; Cl] | 29.77 | 74.82 | NE | 25.07 | NE | 49.60 |
| 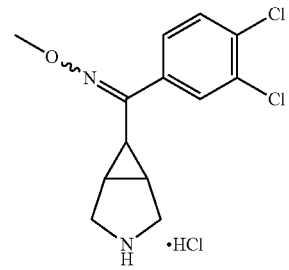 [SMILES: CON=C(c1ccc(Cl)c(Cl)c1)C1C2CNCC21 ; Cl] | 43.09 | 84.85 | 15.59 | 75.59 | — | 32.76 |

TABLE IV-continued

| | In-vitro Data | | | | | |
|---|---|---|---|---|---|---|
| | SERT % Citalopram displacement | | NET % Nisoxetine displacement | | DAT % WIN 35428 displacement | |
| Compound | 100 nM | 1 μM | 100 nM | 1 μM | 100 nM | 1 μM |
| (ethoxyimino 3,4-dichlorophenyl azabicyclic compound ·HCl) | 49.78 | 87.54 | 18.21 | 61.45 | NE | 71.03 |
| (allyloxyimino 3,4-dichlorophenyl azabicyclic compound ·HCl) | 72.58 | 94.40 | 14.35 | 71.29 | NE | 78.02 |
| (cyclopropylmethoxyimino 3,4-dichlorophenyl azabicyclic compound ·HCl) | 69.77 | 95.45 | NE | 33.94 | NE | 68.73 |
| (phenoxyimino 3,4-dichlorophenyl azabicyclic compound ·HCl) | NE | 61.39 | NE | 19.07 | NE | NE |

TABLE IV-continued
In-vitro Data
| Compound | SERT % Citalopram displacement | | NET % Nisoxetine displacement | | DAT % WIN 35428 displacement | |
|---|---|---|---|---|---|---|
| | 100 nM | 1 μM | 100 nM | 1 μM | 100 nM | 1 μM |
| 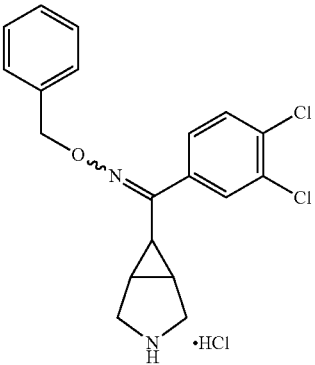 [SMILES: Clc1ccc(C(=NOCc2ccccc2)C2C3CNCC32)cc1Cl ; Cl] | 30.43 | 85.75 | NE | 27.21 | NE | 36.05 |
| 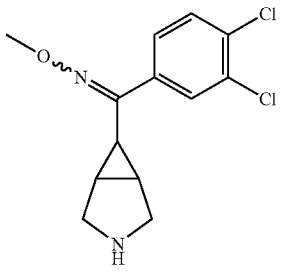 [SMILES: CON=C(c1ccc(Cl)c(Cl)c1)C1C2CNCC21] | 50.25 | 90.07 | 24.48 | 75.97 | 28.11 | 64.58 |
| 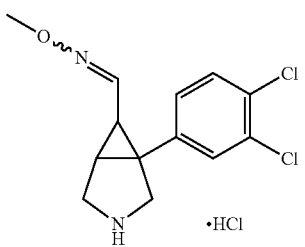 | 64.96 | 91.84 | 37.41 | 82.26 | 30.55 | 66.35 |
| 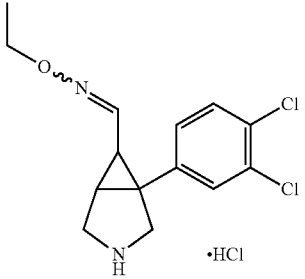 [SMILES: CCON=CC1C2CNCC12c1ccc(Cl)c(Cl)c1 ; Cl] | 83.72 | 94.38 | — | — | 16.74 | 71.76 |

TABLE IV-continued

| | In-vitro Data | | | | | |
|---|---|---|---|---|---|---|
| | SERT % Citalopram displacement | | NET % Nisoxetine displacement | | DAT % WIN 35428 displacement | |
| Compound | 100 nM | 1 μM | 100 nM | 1 μM | 100 nM | 1 μM |
| [structure: benzyloxyimino-3,4-dichlorophenyl bicyclic pyrrolidine·HCl] | 23.26 | 89.03 | 34.60 | 73.56 | 26.96 | 39.02 |
| [structure: 4-fluorobenzyloxyimino-3,4-dichlorophenyl bicyclic pyrrolidine·HCl] | 12.54 | 88.76 | NE | 74.15 | NE | 40.87 |
| [structure: methoxyimino-4-chlorophenyl bicyclic pyrrolidine·HCl] | 37.81 | 85.57 | NE | 54.45 | NE | 29.89 |
| [structure: methoxyimino-4-fluorophenyl bicyclic pyrrolidine·HCl] | 43.52 | 85.13 | NE | NE | NE | NE |

TABLE IV-continued

| | In-vitro Data | | | | | |
|---|---|---|---|---|---|---|
| | SERT % Citalopram displacement | | NET % Nisoxetine displacement | | DAT % WIN 35428 displacement | |
| Compound | 100 nM | 1 μM | 100 nM | 1 μM | 100 nM | 1 μM |
| 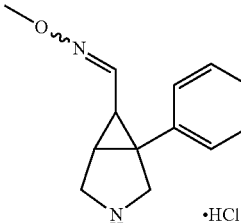 | 39.17 | 79.88 | NE | NE | NE | NE |

NE: Not Effective

The invention claimed is:

1. A compound of Formula I,

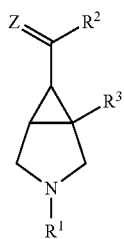

Formula I or its pharmaceutically acceptable salts, tautomeric forms, stereoisomers or polymorphs thereof, wherein:

$R^1$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl; each of which may be optionally substituted at any available position by one or more substituents selected from $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COON, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a$(C=$NR^b$)$NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a$(=$NOR^b$), —$CR^a$(=$NCOOR^b$), —$CR^a$(=$NSOR^b$), —$CR^a$(=$NSO_2R^b$), —C(=$NR^a$)—$NR^bR^c$, —C(=$NOR^a$)—$NR^bR^c$, —$CR^a$(=NCN), —$NCR^a$, —$P(O)R^aR^b$, —$P(O)OR^aOR^b$, —$P(O)R^aOR^b$, —$P(O)NR^aOR^b$, —$P(O)NR^aR^b$, —OP(O) $R^aR^b$, —NHP(O) $R^aR^b$;

with the proviso that when $R^1$ is heterocyclyl, aryl or heteroaryl, then the said heterocyclyl, aryl or heteroaryl cannot be substituted with heterocyclyl;

$R^2$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl; each of which may be optionally substituted at any available position by one or more substituents selected from $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a$(C=$NR^b$)$NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a$(=$NOR^b$), —$CR^a$(=$NCOOR^b$), —$CR^a$(=$NSOR^b$), —$CR^a$(=$NSO_2R^b$), —C(=$NR^a$)—$NR^bR^c$, —C(=$NOR^a$)—$NR^bR^c$, —$CR^a$(=NCN), —$NCR^a$, —$P(O)R^aR^b$, —$P(O)OR^aOR^b$, —$P(O)R^aOR^b$, —$P(O)NR^aOR^b$, —$P(O)NR^aR^b$, —OP(O) $R^aR^b$, —NHP(O) $R^aR^b$;

$R^3$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl; each of which may be optionally substituted at any available position by one or more substituents selected from $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —N(C=NH)$NH_2$, —$NHNH_2$, —NHCHO, —NH- CHS, —NHCOOH, —NHCSOH, —OH, —SH, —SO₃H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO₂R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO₂, —OCSNR$^a$R$^b$, —SR$^a$, —S(O)R$^a$, —S(O)₂R$^a$, —SO₂NR$^a$R$^b$, —CR$^a$(=NOR$^b$), —CR$^a$(=NCOOR$^b$), —CR$^a$(=NSOR$^b$), —CR$^a$(=NSO₂R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O) R$^a$R$^b$, —NHP(O) R$^a$R$^b$;

provided that
(a) atleast one of R² and R³ is aryl or heteroaryl
(b) when R³ is aryl or heteroaryl, then R³ cannot be substituted by heterocyclyl;

Z represents either NOR⁴ or NNR⁴R⁵;

R⁴ and R⁵ are independently selected from —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl; each of which may be optionally substituted at any available position by one or more substituents selected from C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO₂R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO₂, —OCSNR$^a$R$^b$, —SR$^a$, —S(O)R$^a$, —S(O)₂R$^a$, —SO₂NR$^a$R$^b$, —CR$^a$(=NOR$^b$), —CR$^a$(=NCOOR$^b$), —CR$^a$(=NSOR$^b$), —CR$^a$(=NSO₂R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O) R$^a$R$^b$, —NHP(O) R$^a$R$^b$;

or
R⁴ and R⁵ are joined together to form a heterocyclyl;

with the proviso that when Z is NOR⁴, and R⁴ is C$_{1-12}$ alkyl, then R² cannot be heterocyclyl or heteroaryl;

R$^a$, R$^b$, R$^c$ and R$^d$ are independently selected from —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH), —CH(=NCN); wherein alkyl, alkenyl, alkynyl, cycloalkyl, cycloalkenyl, cycloalkynyl, heterocyclyl, aryl and heteroaryl groups may be optionally substituted at any available position by one or more substituents selected from C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N₃, —NO₂, —OCN, —NCO, —SCN, —NCS, —OCONH₂, —ONO₂, —F, —Cl, —Br, —I, —CO—, —CS—, —CHO, —CHS, —COOH, —COSH, —CONH₂, —CONHNH₂, —CSNHNH₂, —CSNH₂, —NH₂, —NHCONH₂, —NHCSNH₂, —N(C=NH)NH₂, —NHNH₂, —NHCHO, —NHCHS, —NHCOOH, —NHCSOH, —OH, —SH, —SO₃H, —CH(=NOH), —CH(=NCN);

or
R$^a$ and R$^b$ are joined together to form a C$_{3-7}$ cycloalkyl, C$_{3-7}$ cycloalkenyl, C$_{6-8}$ cycloalkynyl, heterocyclyl, aryl, heteroaryl;

or
R$^b$ and R$^c$ are joined together to form a C$_{3-7}$ cycloalkyl, C$_{3-7}$ cycloalkenyl, C$_{6-8}$ cycloalkynyl, heterocyclyl, aryl, heteroaryl;

or
R$^c$ and R$^d$ are joined together to form a C$_{3-7}$ cycloalkyl, C$_{3-7}$ cycloalkenyl, C$_{6-8}$ cycloalkynyl, heterocyclyl, aryl, heteroaryl.

2. The compound according to claim 1 having the Formula Ia, wherein

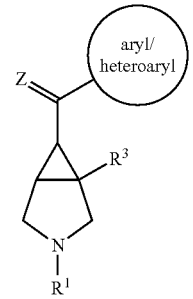

Formula Ia aryl or heteroaryl is unsubstituted or substituted, at any available position, with one or more substituents selected from —F, —Cl, —Br, —I, —OH, —OR$^a$, C$_{1-12}$ alkyl; R¹, R³ and Z are as defined in claim 1; its pharmaceutically acceptable salts, tautomeric forms, stereoisomers or polymorphs thereof.

3. The compound according to claim 1 having the Formula Ib, wherein

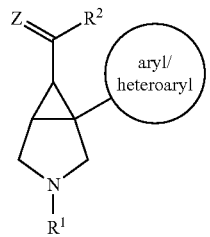

Formula Ib aryl or heteroaryl is unsubstituted or substituted, at any available position, with one or more substituents selected from —F, —Cl, —Br, —I, —OH, —OR$^a$, C$_{1-12}$ alkyl; R$^1$, R$^2$ and Z are as defined in claim 1; or its pharmaceutically acceptable salts, tautomeric forms, stereoisomers or polymorphs thereof.

4. The compound according to claim 1, wherein R$^2$ and R$^3$ are independently selected from —H, C$_{1-12}$ alkyl, C$_{2-12}$ alkenyl, C$_{2-12}$ alkynyl, C$_{3-7}$ cycloalkyl, heterocyclyl, aryl, heteroaryl, each of which is unsubstituted or substituted, at any available position, with one or more substituents selected from —F, —Cl, —Br, —I, —OH, —OR$^a$, C$_{1-12}$ alkyl, C$_{3-7}$ cycloalkyl, aryl, heteroaryl.

5. The compound according to claim 1 wherein R$^3$ is selected from —H,

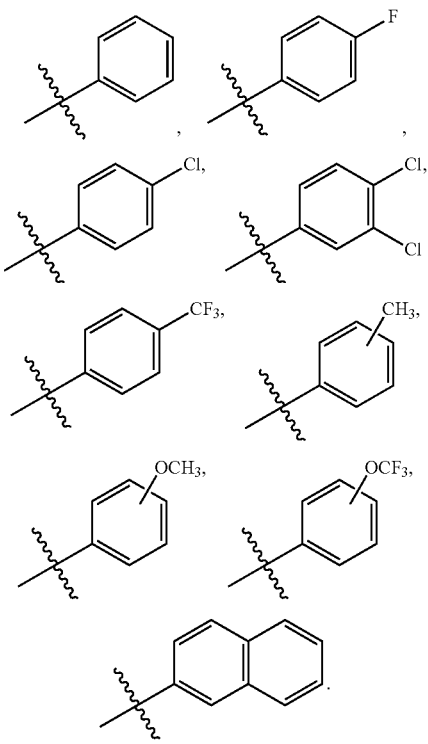

6. The compound according to claim 1 wherein R$^2$ is selected from —H,

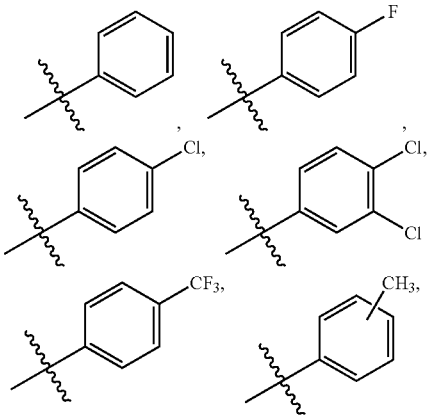

-continued

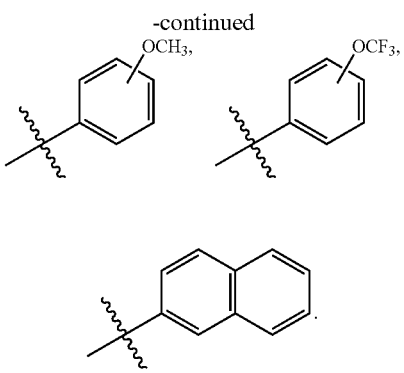

7. The compound according to claim 1 wherein R$^1$ is selected from —H, C$_{1-12}$ alkyl, C$_{2-12}$ alkenyl, C$_{2-12}$ alkynyl, C$_{3-7}$ cycloalkyl, each of which is unsubstituted or substituted, at any available position, with one or more substituents selected from —F, —Cl, —Br, —I, —OH, C$_{3-7}$ cycloalkyl, —OR$^a$.

8. The compound according to claim 1 wherein R$^1$ is —H or C$_{1-12}$ alkyl.

9. The compound according to claim 1 wherein Z is NOR$^4$.

10. The compound according to claim 9, wherein R$^4$ is selected from —H, C$_{1-12}$ alkyl, C$_{2-12}$ alkenyl, C$_{2-12}$ alkynyl, C$_{3-7}$ cycloalkyl, heterocyclyl, aryl, heteroaryl, each of which is unsubstituted or substituted, at any available position, with one or more substituents selected from —F, —Cl, —Br, —I, C$_{3-7}$ cycloalkyl, heterocyclyl, aryl, heteroaryl, —OH, —OR$^a$, —NR$^a$R$^b$; with the proviso that when R$^4$ is C$_{1-12}$ alkyl, then R$^2$ cannot be heterocyclyl or heteroaryl.

11. The compound according to claim 9, wherein R$^4$ is selected from —H, —CH$_3$, —C$_2$H$_5$, —CH$_2$—CH=CH$_2$, —C$_6$H$_5$, —CH$_2$—C$_6$H$_5$, —(CH$_2$)$_2$—OCH$_3$, —(CH$_2$)$_2$—NH$_2$,

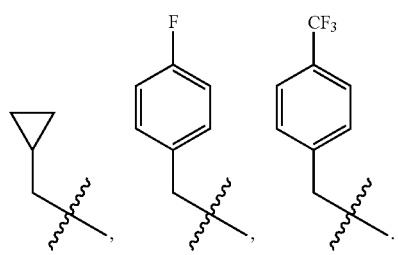 [SMILES: *CC1CC1 ; *Cc1ccc(F)cc1 ; *Cc1ccc(C(F)(F)F)cc1]

12. A compound which is selected from the group consisting of:

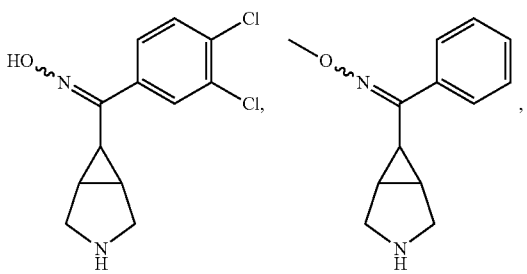

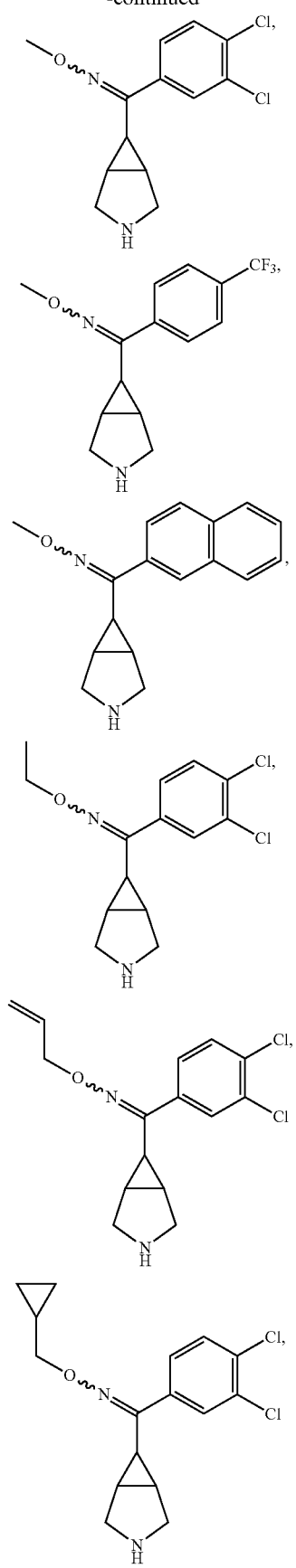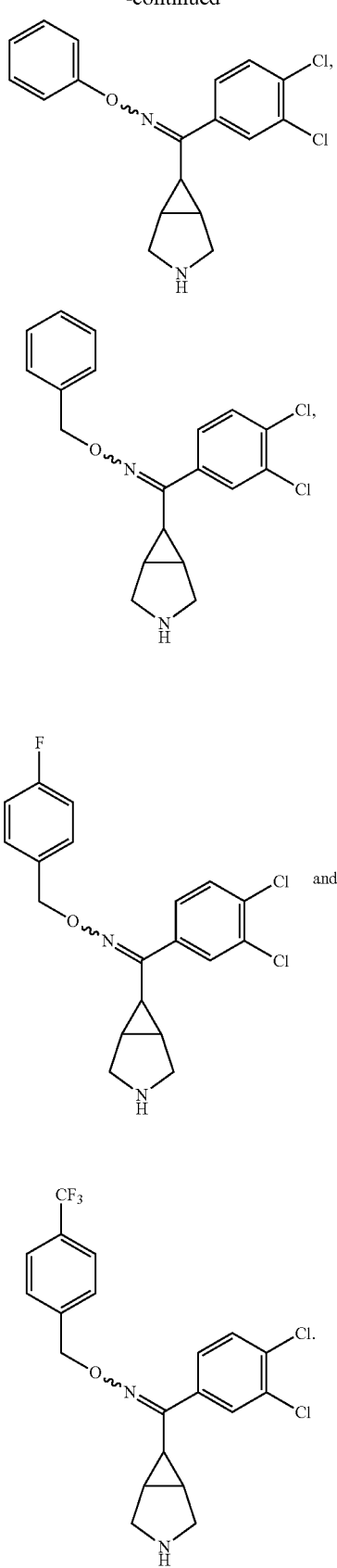

13. A compound which is selected from the group consisting of:

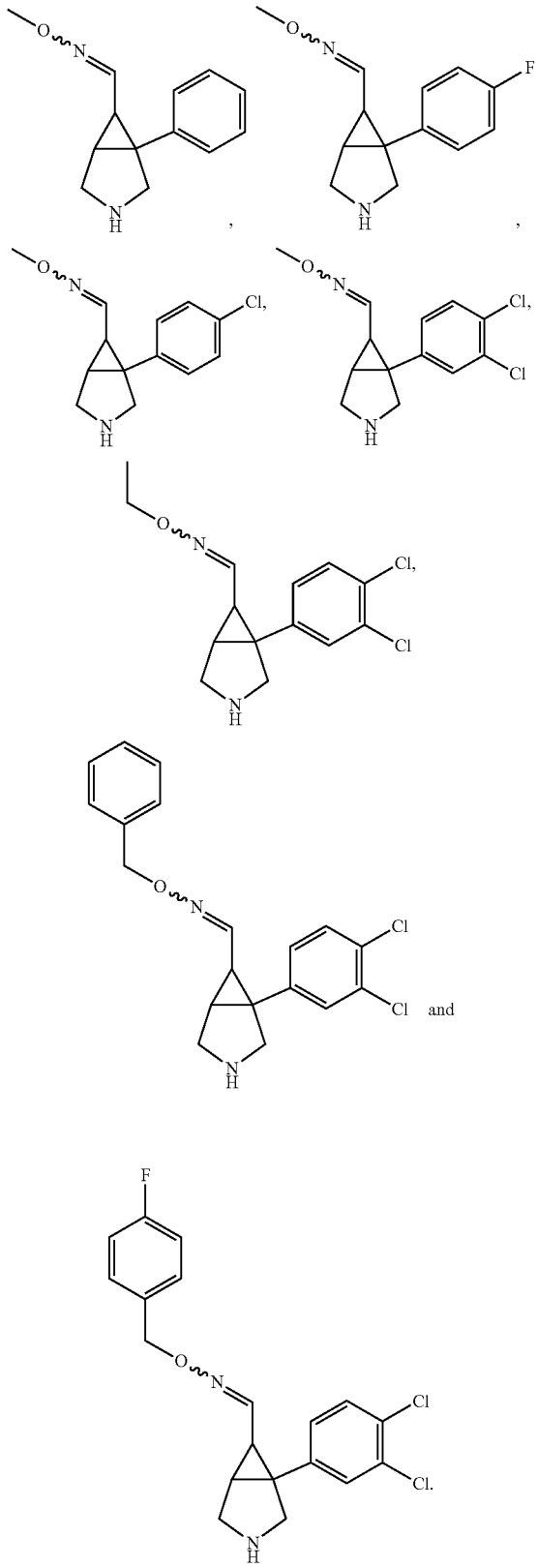

and

14. A compound of Formula V,

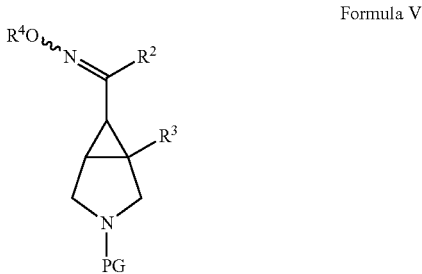

Formula V or its pharmaceutically acceptable salts, tautomeric forms, stereoisomers or polymorphs thereof, wherein:

PG represents protecting group of nitrogen, wherein the protecting group on nitrogen is selected from methyl carbamate, ethyl carbamate, tert-butyl carbamate, benzyl carbamate, 9-fluorenylmethyl carbamate, 2,2,2-trichloroethyl carbamate, 2-phenylethyl carbamate, allyl carbamate, benzyl carbamate, N'-p-toluenesulfonylaminocarbonyl, N-formyl, N-acetyl, N-trifluoroacetyl, N-picolinyl, N-benzoyl, N-methyl, N-allyl, N-acetoxypropyl, N-benzyl, and N-2,7-dichloro-9-fluorenylmethylene;

with the proviso that when PG represents N-(aryl/heterocyclyl/heteroaryl)amine, then the said aryl, heterocyclyl or heteroaryl cannot be substituted with heterocyclyl;

$R^2$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl; each of which may be optionally substituted at any available position by one or more substituents selected from $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —$N(C=NH)NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$CSR^a$, —$COOR^a$, —$CSOR^a$, —$COSR^a$, —$CONR^aR^b$, —$CSNR^aR^b$, —$COCOR^a$, —$CONR^aNR^bR^c$, —$CSNR^aNR^bR^c$, —$CSNR^aR^b$, —$NR^aR^b$, —$NR^aSO_2R^b$, —$NR^aCONR^bR^c$, —$NR^aCSNR^bR^c$, —$NR^a(C=NR^b)NR^cR^d$, —$NR^aNR^bR^c$, —$NR^aCOR^b$, —$NR^aCSR^b$, —$NR^aCOOR^b$, —$NR^aCSOR^b$, =$NOR^a$, —$OR^a$, —$OCOR^a$, —$CSOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a(=NOR^b)$, —$CR^a(=NCOOR^b)$, —$CR^a(=NSOR^b)$, —$CR^a(=NSO_2R^b)$, —$C(=NR^a)$—$NR^bR^c$, —$C(=NOR^a)$—$NR^bR^c$, —$CR^a(=NCN)$, —$NCR^a$, —$P(O)R^aR^b$, —$P(O)OR^aOR^b$, —$P(O)R^aOR^b$, —$P(O)NR^aOR^b$, —$P(O)NR^aR^b$, —$OP(O)R^aR^b$, —$NHP(O)R^aR^b$;

$R^3$ represents —H, $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl; each of which may be optionally substituted at any available position by one or more substituents selected from $C_{1-12}$ alkyl, $C_{2-12}$ alkenyl, $C_{2-12}$ alkynyl, $C_{3-7}$ cycloalkyl, $C_{3-7}$ cycloalkenyl, $C_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O) R$^a$R$^b$, —NHP(O)R$^a$R$^b$;

provided that
(a) atleast one of R$^2$ and R$^3$ is aryl or heteroaryl
(b) when R$^3$ is aryl or heteroaryl, then R$^3$ cannot be substituted by heterocyclyl;

R$^4$ is selected from —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl; each of which may be optionally substituted at any available position by one or more substituents selected from C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, =NOR$^a$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O) R$^a$R$^b$, —NHP(O)R$^a$R$^b$;

with the proviso that when R$^4$ is C$_{1-12}$ alkyl, then R$^2$ cannot be heterocyclyl or heteroaryl;

R$^a$, R$^b$, R$^c$ and R$^d$ are independently selected from —H, C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN); wherein alkyl, alkenyl, alkynyl, cycloalkyl, cycloalkenyl, cycloalkynyl, heterocyclyl, aryl and heteroaryl groups may be optionally substituted at any available position by one or more substituents selected from C$_{1-12}$ alkyl, C$_{2-12}$ alkenyl, C$_{2-12}$ alkynyl, C$_{3-7}$ cycloalkyl, C$_{3-7}$ cycloalkenyl, C$_{6-8}$ cycloalkynyl, heterocyclyl, aryl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN);

or

R$^a$ and R$^b$ are joined together to form a C$_{3-7}$ cycloalkyl, C$_{3-7}$ cycloalkenyl, C$_{6-8}$ cycloalkynyl, heterocyclyl, aryl, heteroaryl;

or

R$^b$ and R$^c$ are joined together to form a C$_{3-7}$ cycloalkyl, C$_{3-7}$ cycloalkenyl, C$_{6-8}$ cycloalkynyl, heterocyclyl, aryl, heteroaryl;

or

R$^c$ and R$^d$ are joined together to form a C$_{3-7}$ cycloalkyl, C$_{3-7}$ cycloalkenyl, C$_{6-8}$ cycloalkynyl, heterocyclyl, aryl, heteroaryl.

15. A pharmaceutical composition, comprising a compound according to claim 1 or its pharmaceutically acceptable salts, derivatives, tautomeric forms, stereoisomers or polymorphs thereof, in combination with one or more pharmaceutically acceptable carrier(s).

16. A pharmaceutical composition, comprising a compound according to claim 14 or its pharmaceutically acceptable salts, tautomeric forms, stereoisomers or polymorphs thereof, in combination with one or more pharmaceutically acceptable carrier(s).

17. A method for prophylaxis, amelioration and/or treatment of one or more condition(s)/disease(s)/disorder(s) of the central and/or peripheral nervous system, in a subject in need thereof, which comprises administering a therapeutically effective amount of compound according to claim 14.

18. A method for prophylaxis, amelioration and/or treatment of one or more condition(s)/disease(s)/disorder(s) of the central and/or peripheral nervous system, in a subject in need thereof, which comprises administering a therapeutically effective amount of compound according to claim 1 or its pharmaceutically acceptable salts, tautomeric forms, stereoisomers, or polymorphs thereof.

19. A method of making a pharmaceutical composition, comprising mixing a compound according to claim 14 or its pharmaceutically acceptable salts, tautomeric forms, stereoisomers or polymorphs thereof, with one or more pharmaceutically acceptable carrier(s).

20. A method of making a pharmaceutical composition, comprising mixing a compound according to claim 1 or its pharmaceutically acceptable salts, tautomeric forms, stereoisomers or polymorphs thereof, with one or more pharmaceutically acceptable carrier(s).

* * * * *